(12) United States Patent
Hendricks et al.

(10) Patent No.: US 10,093,969 B2
(45) Date of Patent: *Oct. 9, 2018

(54) ENHANCED LIGATION REACTIONS

(71) Applicant: Life Technologies Corporation, Carlsbad, CA (US)

(72) Inventors: Stephen Hendricks, Los Gatos, CA (US); David King, San Francisco, CA (US); Lei Xi, Foster City, CA (US); Marian Peris, San Mateo, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/695,244

(22) Filed: Sep. 5, 2017

(65) Prior Publication Data

US 2018/0010177 A1    Jan. 11, 2018

Related U.S. Application Data

(63) Continuation of application No. 15/071,086, filed on Mar. 15, 2016, now Pat. No. 9,765,388, which is a continuation of application No. 14/360,892, filed as application No. PCT/US2012/066869 on Nov. 28, 2012, now Pat. No. 9,315,861, and a continuation of application No. 13/980,280, filed as application No. PCT/US2012/021465 on Jan. 17, 2012.

(60) Provisional application No. 61/564,243, filed on Nov. 28, 2011, provisional application No. 61/433,488, filed on Jan. 17, 2011, provisional application No. 61/433,502, filed on Jan. 17, 2011, provisional application No. 61/474,168, filed on Apr. 11, 2011, provisional application No. 61/474,205, filed on Apr. 11, 2011.

(51) Int. Cl.
| | | |
|---|---|---|
| *C12Q 1/68* | (2018.01) | |
| *C12Q 1/6853* | (2018.01) | |
| *C12P 19/34* | (2006.01) | |
| *C12Q 1/6874* | (2018.01) | |
| *C12Q 1/6869* | (2018.01) | |
| *C12Q 1/6834* | (2018.01) | |
| *C12Q 1/6844* | (2018.01) | |
| *C12Q 1/46* | (2006.01) | |

(52) U.S. Cl.
CPC ............ *C12Q 1/6853* (2013.01); *C12P 19/34* (2013.01); *C12Q 1/46* (2013.01); *C12Q 1/6834* (2013.01); *C12Q 1/6846* (2013.01); *C12Q 1/6869* (2013.01); *C12Q 1/6874* (2013.01)

(58) Field of Classification Search
None
See application file for complete search history.

(56) References Cited

U.S. PATENT DOCUMENTS

| | | |
|---|---|---|
| 4,883,750 A | 11/1989 | Whiteley et al. |
| 4,988,617 A | 1/1991 | Landegren et al. |
| 5,426,180 A | 6/1995 | Kool |
| 5,476,930 A | 12/1995 | Letsinger et al. |
| 5,593,826 A | 1/1997 | Fung et al. |
| 5,871,921 A | 2/1999 | Landegren et al. |
| 7,255,994 B2 | 8/2007 | Lao |
| 2004/0110213 A1 | 6/2004 | Namsaraev |
| 2009/0026082 A1* | 1/2009 | Rothberg ............. C12Q 1/6869 204/556 |
| 2010/0081140 A1 | 4/2010 | Church et al. |
| 2011/0104785 A1 | 5/2011 | Vaidyanathan et al. |

FOREIGN PATENT DOCUMENTS

| | | | |
|---|---|---|---|
| WO | 1997031256 | 8/1997 | |
| WO | 2001092579 | 12/2001 | |
| WO | 2007121489 | 10/2007 | |
| WO | 2009/149915 | 12/2009 | |
| WO | WO-2009149915 A1 * | 12/2009 | ............... C12Q 1/25 |
| WO | 2010/111686 A2 | 9/2010 | |
| WO | 2012/099832 A2 | 7/2012 | |

OTHER PUBLICATIONS

Odell and Shuman (Footprinting of Chlorella Virus DNA Ligase Bound at a Nick in Duplex DNA, The Journal of Biological Chemistry 274, 14032-14039, May 14, 1999).*
Bornhorst et al. (Purification of Proteins Using Polyhistidine Affinity Tags, Ch. 16 in Methods Enzymol. 2000; 326: 245-254, available in PMC Jul. 25, 2010).*
Ahel, Ivan et al., "The neurodegenerative disease protein aprataxin resolves abortive DNA ligation intermediates", Nature, vol. 443, No. 7112, 2006, 713-716.
Altschul, Stephen F. et al., "Gapped BLAST and PSI-BLAST: a new generation of protein database search", Nucleic Acids Research, vol. 25, No. 17, Sep. 1997, 3389-3402.
Barany, et al., "Genetic Disease Detection and DNA Amplification Using Cloned Thermostable Ligase", Proceedings of the National Academy of Sciences, vol. 88, Issue 1, 1991, 189-193.
Bi, W et al., "CCR: a rapid and simple approach for mutation detection", Nucl. Acids Res., vol. 25(14), 1997, pp. 2949-2951.
Brenner, Charles, "Hint, Fhit and GalT: Function, Structure, Evolution and Mechanism of Three Branches of the Histidine Triad Superfamily of Nucleotide Hydrolases and Transferases", Biochemistry, Jul. 23, 2002; 41(29): 9003-9014.

(Continued)

Primary Examiner — Aaron A Priest

(57) ABSTRACT

In some embodiments, methods for ligating nucleic acid ends comprise: conducting a nucleic acid ligation reaction in the presence of at least one agent that generates a ligatable terminal 5' phosphate group by removing an adenylate group from a terminal 5' phosphate of a nucleic acid. In some embodiments, an aprataxin enzyme can catalyze removal of an adenylate group from a terminal 5' phosphate of a nucleic acid. In some embodiments, methods for ligating nucleic acid ends comprise: conducting a nucleic acid ligation reaction in the presence of an aprataxin enzyme under conditions suitable for ligating nucleic acid ends.

19 Claims, 4 Drawing Sheets

Specification includes a Sequence Listing.

(56) References Cited

OTHER PUBLICATIONS

Creighton, et al., "Proteins: Structures and Molecular Principles", W.H. Freeman & Company, Apr. 1984.
Engler, M. J, et al., "DNA Ligases", The Enzymes, 15, 1982, 3-29.
Fasman, Gerald D., "UV Spectral Characteristics and Acidic Dissociation Constants of 280 Alkyl Bases. Nucleosides and Nucleotides", Practical Handbook of Biochemistry and Molecular Biology, CRC Press, Boca Raton, FL, 1989, pp. 385-394.
Grossman, et al., "High-Density Multiplex Detection of Nucleic Acid Sequences: Oligonucleotide Ligation Assay and Sequence-Coded Separation", Nucleic Acids Research: vol. 22(21), 1994, 4527-4534.
Higgins, N. Patrick et al., "DNA-Joining Enzymes: A Review", Methods in Enzymology, vol. 68, 1979, 50-71.
Ho, C. Kiong et al., "Characterization of an ATP-Dependent DNA Ligase Encoded by Chlorella Virus PBCV-1", Journal of Virology, Vo. 71, No. 3, 1997, 1931-1937.
Landegren, et al., "A Ligase-Mediated Gene Detection Techniaue", Science 241, vol. 241, 1988, 1077-1080.
Landegren, U., "Ligation-based DNA Diagnostics", Bioessays, 15(11), 1993, 761-765.
Nakatani, et al., "Substrate recognition and fidelity of strand joining by an archaeal DNA ligase", Eur. J. Biochem., vol. 269, No. 2, 2002, 650-656.
Needleman, et al., "Needleman-Wunsch Algorithm for Sequence Similarity Searches", J. Mol. Biol., 48, 1970, 443.
Odell, Mark et al., "Analysis of the DNA joining repertoire of Chlorella virus DNA ligase and a new crystal structure of the ligase-adenylate intermediate", Nucl. Acids Res., 31(17), 2003, 5090-5100.
Odell, Mark, et al., "Footprinting of Chlorella virus DNA ligase bound at a nick in duplex DNA", J Biol Chem., May 14, 1991:274(20):14032-14039.
PCT/US2012/021465, International Preliminary Report on Patentability dated Jul. 17, 2013, 11 pages.
PCT/US2012/021465, International Search Report and Written Opinion dated Aug. 27, 2012, 17 pages.
PCT/US2012/021465, Invitation to Pay Additional Fees dated Jun. 12, 2012, 8 pages.
PCT/US2012/066869, International Search Report and Written Opinion dated Feb. 8, 2013.
Pritchard, Clare et al., "Effects of base mismatches on joining of short oligodeoxynucleotides by DNA ligases", Nucleic Acids Research, Oxford University Press, Surrey, GB, vol. 25, No. 17, 1997, 3403-3407.
Rass, Ulrich et al., "Actions of Aprataxin in Multiple DNA Repair Pathways", Journal of Biological Chemistry, vol. 282, No. 13, 2007, 9469-9474.
Rass, Ulrich et al., "Molecular Mechanism of DNA Deadenylation by the Neurological Disease Protein Aprataxin", Journal of Biological Chemistry, vol. 283, No. 49, 2008, 33994-34001.
Skobeltsyna, Larisa et al., "Short Oligonucleotide Tandem Ligation Assay for Genotyping of Single-Nucleotide Polymorphisms in Y Chromosome", Molecular Biotechnology, vol. 45, No. 1, 2010, 1-8.
Smith, Temple F. et al., "Comparison of biosequences", Advances in Applied Mathematics, vol. 2, No. 4, 1981, 482-489.
Xu, Y et al., "High sequence fidelity in a non-enzymatic DNA autoligation reation", Nucl. Acids Res., vol. 27(3), 1999, pp. 875-881.
Zirvi, M et al., "Ligase-Based Detection ofMononucleotide Repeat Sequences", Nuc Acids Res.vol. 27(24), 1999, pp. e40i-e40viii.

* cited by examiner

MMRVCWLVRQDSRHQRIRLPHLEAVVIGRGPETKITDKKCSRQQVQLKAE
CNKGYVKVKQVGVNPTSIDSVVIGKDQEVKLQPGQVLHMVNELYPYIVEF
EEEAKNPGLETHRKRKRSGNSDSIERDAAQEAEAGTGLEPGSNSGQCSVP
LKKGKDAPIKKESLGHWSQGLKISMQDPKMQVYKDEQVVVIKDKYPKARY
HWLVLPWTSISSLKAVAREHLELLKHMHTVGEKVIVDFAGSSKLRFRLGY
HAIPSMSHVHLHVISQDFDSPCLKNKKHWNSFNTEYFLESQAVIEMVQEA
GRVTVRDGMPELLKLPLRCHECQQLLPSIPQLKEHLRKHWTQHHHHHHHH

FIG. 2A

ATGATGCGTGTGTGCTGGTTGGTGCGCCAGGACAGCCGTCACCAGCGTAT
CCGCCTTCCACATTTGGAAGCAGTTGTGATTGGTCGTGGCCCAGAGACCA
AGATCACTGATAAGAAATGTTCGCGTCAGCAAGTTCAGTTGAAAGCAGAG
TGTAACAAGGGTTATGTCAAGGTCAAGCAGGTGGGTGTCAATCCGACCAG
CATTGACAGTGTCGTTATTGGCAAGGACCAAGAGGTGAAGCTGCAGCCGG
GCCAGGTTCTCCACATGGTGAATGAACTTTATCCATATATTGTCGAGTTT
GAGGAAGAGGCAAAGAACCCTGGCCTGGAAACGCACCGCAAGCGCAAGCG
CAGCGGCAACAGTGATTCTATCGAACGCGATGCGGCGCAGGAAGCCGAGG
CGGGGACGGGCCTGGAACCTGGGAGCAACTCGGGCCAATGCTCTGTGCCG
TTAAAGAAGGGTAAAGATGCACCTATCAAAAAGGAATCCCTGGGCCACTG
GAGTCAAGGCTTGAAGATTTCTATGCAGGACCCGAAAATGCAGGTTTACA
AAGATGAGCAGGTGGTGGTGATTAAGGATAAATACCCAAAGGCCCGTTAC
CATTGGCTGGTCTTACCGTGGACCTCCATTTCCAGTCTGAAGGCGGTGGC
CCGTGAACACCTTGAACTCCTTAAGCATATGCACACTGTGGGGGAAAAGG
TGATTGTTGATTTTGCGGGGTCCAGCAAACTCCGCTTCCGTTTGGGCTAC
CACGCCATTCCGAGTATGAGCCATGTGCATCTTCATGTGATCAGCCAGGA
TTTTGATTCTCCTTGCCTTAAAAACAAAAACATTGGAACTCGTTCAATA
CGGAATACTTCTTAGAATCACAAGCGGTGATCGAGATGGTTCAAGAGGCT
GGTCGCGTAACTGTCCGTGATGGGATGCCGGAGCTCTTGAAGCTGCCGCT
TCGTTGTCATGAGTGCCAGCAGCTGCTGCCTTCCATTCCTCAGCTGAAAG
AACATCTCCGCAAGCACTGGACGCAGcatcaccatcaccatcaccatcac
Taa

FIG. 2B

CV DNA Ligase, GenBank ID AAC96909.1, from Paramecium bursaria
Chlorella virus 1:

MAITKPLLAATLENIEDVQFPCLATPKIDGIRSVKQTQMLSRTFKPIRNSVMNRLLTELLPEGSD
GEISIEGATFQDTTSAVMTGHKMYNAKFSYYWFDYVTDDPLKKYIDRVEDMKNYITVHPHILEHA
QVKIIPLIPVEINNITELLQYERDVLSKGFEGVMIRKPDGKYKFGRSTLKEGILLKMKQFKDAEA
TIISMTALFKNTNTKTKDNFGYSKRSTHKSGKVEEDVMGSIEVDYDGVVFSIGTGFDADQRRDFW
QNKESYIGKMVKFKYFEMGSKDCPRFPVFIGIRHEEDR

FIG. 3

MnM DNA Ligase, GenBank ID YP_333052.1, from Burkholderia
pseudomallei 1710b (equivalent sequence to ABA50091)

MSGVPYGFKPNLAATLTKPELIKFPVWASPKIDGIRCVFFGGVAYSRSLKPIPNPVVQEFAKAYA
NLLEGLDGELTVGSPTDANCMQNSMAVMSKAAAPDFTFHVFDWFHPAQAHIEFWQRSDVVEDRIV
QFYDRYPEVDIRAAPQVLCTSLAHLDTNEARWLADGYEGMMIRDHCGRYKFGRSTEREGGLVKVK
RFTDAEAIVIGFEEEMHNANEAKRDATGRTERSTSKAGLHGKGTLGALVVKNERGIVFNIGTGFT
AAQRADYWANHPSLFGKMVKFKHFDHGTVDAPRHPVFIGFRHPEDM

FIG. 4

Hin DNA Ligase, GenBank ID P44121, from Haemophilus influenza

MKFYRTLLLFFASSFAFANSDLMLLHTYNNQPIEGWVMSEKLDGVRGYWNGKQLLTRQGQRLSPP
AYFIKDFPPFAIDGELFSERNHFEEISTITKSFKGDGWEKLKLYVFDVPDAEGNLFERLAKLKAH
LLEHPTTYIEIIEQIPVKDKTHLYQFLAQVENLQGEGVVVRNPNAPYERKRSSQILKLKTARGEE
CTVIAHHKGKGQFENVMGALTCKNHRGEFKIGSGFNLNERENPPPIGSVITYKYRGITNSGKPRF
ATYWREKK

FIG. 5

DLX DNA Ligase, artificial ligase derived from Hin DNA ligase
from Haemophilus influenza:

MKFYRTLLLFFASSFAFANSDLMLLHTYNNQPIEGWVMSEKLDGVRGYWNGKQLLTRQGQRLSPP
AYFIKDFPPFAIDGELFSERNHFEEISSITKSFKGDGWEKLKLYVFDVPDAEGNLFERLAKLKAH
LLEHPTTYIEIIEQIPVKDKTHLYQFLAQVENLQGEGVVVRNPNAPYERKRSSQILKLKTARGEE
CTVIAHHKGKGQFENVMGALTCKNHRGEFKIGSGFNLNERENPPPIGSVITYKYRGITNSGKPRF
ATYWREKK

FIG. 6

DLXd DNA Ligase, artificial ligase derived from Hin D ligase from
Haemophilus influenza:

MKFYRTLLLFFASSFAFANSDLMLLHTYNNQPIEGWVMSEKLDGVRGYWNGKQLLTRQGQRLSPP
AYFIKDFPPFAIDGELFSERNHFEEISSITKSFKGDGWEKLKLYVFDVPDAEGNLFERLAKLKAH
LLEHPTTYIEIIEQIPVKDKTHLYQFLAQVENLQGEGVVVRNPNAPYERKRSSQILKLKTARDEE
CTVIAHHKGKGQFENVMGALTCKNHRGEFKIGSGFNLNERENPPPIGSVITYKYRGITNSGKPRF
ATYWREKK

FIG. 7

DLXd2 DNA Ligase (Gammaproteobacteria, Haemophilus influenza)
(modified)

MLLHTYNNQPIEGWVMSEKLDGVRGYWNGKQLLTRQGQRLSPPAYFIKDFPPFAIDGELFSERNH
FEEISSITKSFKGDGWEKLKLYVFDVPDAEGNLFERLAKLKAHLLEHPTTYIEIIEQIPVKDKTH
LYQFLAQVENLQGEGVVVRNPNAPYERKRSSQILKLKTARDEECTVIAHHKGKGQFENVMGALTC
KNHRGEFKIGSGFNLNERENPPPIGSVITYKYRGITNSGKPRFATYWREKK

FIG. 8

SEQUENCE LISTING

```
<160> NUMBER OF SEQ ID NOS: 8

<210> SEQ ID NO 1
<211> LENGTH: 350
<212> TYPE: PRT
<213> ORGANISM: Artificial Sequence
<220> FEATURE:
<223> OTHER INFORMATION: amino acids sequence of human aprataxin enzyme

<400> SEQUENCE: 1

Met Met Arg Val Cys Trp Leu Val Arg Gln Asp Ser Arg His Gln Arg
1               5                   10                  15

Ile Arg Leu Pro His Leu Glu Ala Val Val Ile Gly Arg Gly Pro Glu
            20                  25                  30

Thr Lys Ile Thr Asp Lys Lys Cys Ser Arg Gln Gln Val Gln Leu Lys
        35                  40                  45

Ala Glu Cys Asn Lys Gly Tyr Val Lys Val Lys Gln Val Gly Val Asn
    50                  55                  60

Pro Thr Ser Ile Asp Ser Val Val Ile Gly Lys Asp Gln Glu Val Lys
65                  70                  75                  80

Leu Gln Pro Gly Gln Val Leu His Met Val Asn Glu Leu Tyr Pro Tyr
                85                  90                  95

Ile Val Glu Phe Glu Glu Glu Ala Lys Asn Pro Gly Leu Glu Thr His
            100                 105                 110

Arg Lys Arg Lys Arg Ser Gly Asn Ser Asp Ser Ile Glu Arg Asp Ala
        115                 120                 125

Ala Gln Glu Ala Glu Ala Gly Thr Gly Leu Glu Pro Gly Ser Asn Ser
    130                 135                 140

Gly Gln Cys Ser Val Pro Leu Lys Lys Gly Lys Asp Ala Pro Ile Lys
145                 150                 155                 160

Lys Glu Ser Leu Gly His Trp Ser Gln Gly Leu Lys Ile Ser Met Gln
                165                 170                 175

Asp Pro Lys Met Gln Val Tyr Lys Asp Glu Gln Val Val Val Ile Lys
            180                 185                 190

Asp Lys Tyr Pro Lys Ala Arg Tyr His Trp Leu Val Leu Pro Trp Thr
        195                 200                 205

Ser Ile Ser Ser Leu Lys Ala Val Ala Arg Glu His Leu Glu Leu Leu
    210                 215                 220

Lys His Met His Thr Val Gly Glu Lys Val Ile Val Asp Phe Ala Gly
225                 230                 235                 240

Ser Ser Lys Leu Arg Phe Arg Leu Gly Tyr His Ala Ile Pro Ser Met
                245                 250                 255

Ser His Val His Leu His Val Ile Ser Gln Asp Phe Asp Ser Pro Cys
            260                 265                 270
```

```
Leu Lys Asn Lys Lys His Trp Asn Ser Phe Asn Thr Glu Tyr Phe Leu
            275                 280                 285

Glu Ser Gln Ala Val Ile Glu Met Val Gln Glu Ala Gly Arg Val Thr
        290                 295                 300

Val Arg Asp Gly Met Pro Glu Leu Leu Lys Leu Pro Leu Arg Cys His
305                 310                 315                 320

Glu Cys Gln Gln Leu Leu Pro Ser Ile Pro Gln Leu Lys Glu His Leu
                325                 330                 335

Arg Lys His Trp Thr Gln His His His His His His
            340                 345                 350
```

```
<210> SEQ ID NO 2
<211> LENGTH: 1053
<212> TYPE: DNA
<213> ORGANISM: Artificial Sequence
<220> FEATURE:
<223> OTHER INFORMATION: nucleotide sequence of a human aprataxin enzyme

<400> SEQUENCE: 2
atgatgcgtg tgtgctggtt ggtgcgccag gacagccgtc accagcgtat ccgccttcca      60
catttggaag cagttgtgat tggtcgtggc ccagagacca agatcactga taagaaatgt     120
tcgcgtcagc aagttcagtt gaaagcagag tgtaacaagg gttatgtcaa ggtcaagcag     180
gtgggtgtca atccgaccag cattgacagt gtcgttattg gcaaggacca agaggtgaag     240
ctgcagccgg gccaggttct ccacatggtg aatgaacttt atccatatat tgtcgagttt     300
gaggaagagg caaagaaccc tggcctggaa acgcaccgca agcgcaagcg cagcggcaac     360
agtgattcta tcgaacgcga tgcggcgcag gaagccgagg cggggacggg cctggaacct     420
gggagcaact cgggccaatg ctctgtgccg ttaaagaagg gtaaagatgc acctatcaaa     480
aaggaatccc tgggccactg gagtcaaggc ttgaagattt ctatgcagga cccgaaaatg     540
caggtttaca aagatgagca ggtggtggtg attaaggata aatacccaaa ggcccgttac     600
cattggctgg tcttaccgtg gacctccatt tccagtctga aggcggtggc ccgtgaacac     660
cttgaactcc ttaagcatat gcacactgtg ggggaaaagg tgattgttga ttttgcgggg     720
tccagcaaac tccgcttccg tttgggctac cacgccattc cgagtatgag ccatgtgcat     780
cttcatgtga tcagccagga ttttgattct ccttgcctta aaacaaaaaa acattggaac     840
tcgttcaata cggaatactt cttagaatca caagcggtga tcgagatggt tcaagaggct     900
ggtcgcgtaa ctgtccgtga tgggatgccg gagctcttga agctgccgct tcgttgtcat     960
gagtgccagc agctgctgcc ttccattcct cagctgaaag aacatctccg caagcactgg    1020
acgcagcatc accatcacca tcaccatcac taa                                 1053
```

```
<210> SEQ ID NO 3
<211> LENGTH: 298
<212> TYPE: PRT
<213> ORGANISM: Paramecium bursaria Chlorella virus 1

<400> SEQUENCE: 3

Met Ala Ile Thr Lys Pro Leu Leu Ala Ala Thr Leu Glu Asn Ile Glu
1               5                   10                  15

Asp Val Gln Phe Pro Cys Leu Ala Thr Pro Lys Ile Asp Gly Ile Arg
            20                  25                  30

Ser Val Lys Gln Thr Gln Met Leu Ser Arg Thr Phe Lys Pro Ile Arg
        35                  40                  45
```

```
Asn Ser Val Met Asn Arg Leu Leu Thr Glu Leu Leu Pro Glu Gly Ser
     50                  55                  60

Asp Gly Glu Ile Ser Ile Glu Gly Ala Thr Phe Gln Asp Thr Thr Ser
 65                  70                  75                  80

Ala Val Met Thr Gly His Lys Met Tyr Asn Ala Lys Phe Ser Tyr Tyr
                 85                  90                  95

Trp Phe Asp Tyr Val Thr Asp Pro Leu Lys Lys Tyr Ile Asp Arg
                100                 105                 110

Val Glu Asp Met Lys Asn Tyr Ile Thr Val His Pro His Ile Leu Glu
                115                 120                 125

His Ala Gln Val Lys Ile Ile Pro Leu Ile Pro Val Glu Ile Asn Asn
130                 135                 140

Ile Thr Glu Leu Leu Gln Tyr Glu Arg Asp Val Leu Ser Lys Gly Phe
145                 150                 155                 160

Glu Gly Val Met Ile Arg Lys Pro Asp Gly Lys Tyr Lys Phe Gly Arg
                165                 170                 175

Ser Thr Leu Lys Glu Gly Ile Leu Leu Lys Met Lys Gln Phe Lys Asp
                180                 185                 190

Ala Glu Ala Thr Ile Ile Ser Met Thr Ala Leu Phe Lys Asn Thr Asn
                195                 200                 205

Thr Lys Thr Lys Asp Asn Phe Gly Tyr Ser Lys Arg Ser Thr His Lys
210                 215                 220

Ser Gly Lys Val Glu Glu Asp Val Met Gly Ser Ile Glu Val Asp Tyr
225                 230                 235                 240

Asp Gly Val Val Phe Ser Ile Gly Thr Gly Phe Asp Ala Asp Gln Arg
                245                 250                 255

Arg Asp Phe Trp Gln Asn Lys Glu Ser Tyr Ile Gly Lys Met Val Lys
                260                 265                 270

Phe Lys Tyr Phe Glu Met Gly Ser Lys Asp Cys Pro Arg Phe Pro Val
                275                 280                 285

Phe Ile Gly Ile Arg His Glu Glu Asp Arg
                290                 295
```

<210> SEQ ID NO 4
<211> LENGTH: 306
<212> TYPE: PRT
<213> ORGANISM: Burkholderia pseudomallei

<400> SEQUENCE: 4

```
Met Ser Gly Val Pro Tyr Gly Phe Lys Pro Asn Leu Ala Ala Thr Leu
 1               5                  10                  15

Thr Lys Pro Glu Leu Ile Lys Phe Pro Val Trp Ala Ser Pro Lys Ile
                20                  25                  30

Asp Gly Ile Arg Cys Val Phe Gly Gly Val Ala Tyr Ser Arg Ser
                35                  40                  45

Leu Lys Pro Ile Pro Asn Pro Val Val Gln Glu Phe Ala Lys Ala Tyr
     50                  55                  60

Ala Asn Leu Leu Glu Gly Leu Asp Gly Glu Leu Thr Val Gly Ser Pro
 65                  70                  75                  80

Thr Asp Ala Asn Cys Met Gln Asn Ser Met Ala Val Met Ser Lys Ala
                 85                  90                  95

Ala Ala Pro Asp Phe Thr Phe His Val Phe Asp Trp Phe His Pro Ala
                100                 105                 110

Gln Ala His Ile Glu Phe Trp Gln Arg Ser Asp Val Val Glu Asp Arg
                115                 120                 125
```

```
Ile Val Gln Phe Tyr Asp Arg Tyr Pro Glu Val Asp Ile Arg Ala Ala
130                 135                 140

Pro Gln Val Leu Cys Thr Ser Leu Ala His Leu Asp Thr Asn Glu Ala
145                 150                 155                 160

Arg Trp Leu Ala Asp Gly Tyr Glu Gly Met Met Ile Arg Asp His Cys
                165                 170                 175

Gly Arg Tyr Lys Phe Gly Arg Ser Thr Glu Arg Glu Gly Gly Leu Val
            180                 185                 190

Lys Val Lys Arg Phe Thr Asp Ala Glu Ala Ile Val Ile Gly Phe Glu
        195                 200                 205

Glu Glu Met His Asn Ala Asn Glu Ala Lys Arg Asp Ala Thr Gly Arg
210                 215                 220

Thr Glu Arg Ser Thr Ser Lys Ala Gly Leu His Gly Lys Gly Thr Leu
225                 230                 235                 240

Gly Ala Leu Val Val Lys Asn Glu Arg Gly Ile Val Phe Asn Ile Gly
                245                 250                 255

Thr Gly Phe Thr Ala Ala Gln Arg Ala Asp Tyr Trp Ala Asn His Pro
            260                 265                 270

Ser Leu Phe Gly Lys Met Val Lys Phe Lys His Phe Asp His Gly Thr
        275                 280                 285

Val Asp Ala Pro Arg His Pro Val Phe Ile Gly Phe Arg His Pro Glu
290                 295                 300

Asp Met
305

<210> SEQ ID NO 5
<211> LENGTH: 268
<212> TYPE: PRT
<213> ORGANISM: Haemophilus influenzae

<400> SEQUENCE: 5

Met Lys Phe Tyr Arg Thr Leu Leu Leu Phe Ala Ser Ser Phe Ala
1               5                   10                  15

Phe Ala Asn Ser Asp Leu Met Leu Leu His Thr Tyr Asn Asn Gln Pro
                20                  25                  30

Ile Glu Gly Trp Val Met Ser Glu Lys Leu Asp Gly Val Arg Gly Tyr
            35                  40                  45

Trp Asn Gly Lys Gln Leu Leu Thr Arg Gln Gly Gln Arg Leu Ser Pro
        50                  55                  60

Pro Ala Tyr Phe Ile Lys Asp Phe Pro Pro Phe Ala Ile Asp Gly Glu
65                  70                  75                  80

Leu Phe Ser Glu Arg Asn His Phe Glu Glu Ile Ser Thr Ile Thr Lys
                85                  90                  95

Ser Phe Lys Gly Asp Gly Trp Glu Lys Leu Lys Leu Tyr Val Phe Asp
            100                 105                 110

Val Pro Asp Ala Glu Gly Asn Leu Phe Glu Arg Leu Ala Lys Leu Lys
        115                 120                 125

Ala His Leu Leu Glu His Pro Thr Thr Tyr Ile Glu Ile Ile Glu Gln
130                 135                 140

Ile Pro Val Lys Asp Lys Thr His Leu Tyr Gln Phe Leu Ala Gln Val
145                 150                 155                 160

Glu Asn Leu Gln Gly Glu Gly Val Val Val Arg Asn Pro Asn Ala Pro
                165                 170                 175

Tyr Glu Arg Lys Arg Ser Ser Gln Ile Leu Lys Leu Lys Thr Ala Arg
            180                 185                 190
```

```
Gly Glu Glu Cys Thr Val Ile Ala His His Lys Gly Lys Gly Gln Phe
            195                 200                 205

Glu Asn Val Met Gly Ala Leu Thr Cys Lys Asn His Arg Gly Glu Phe
    210                 215                 220

Lys Ile Gly Ser Gly Phe Asn Leu Asn Glu Arg Glu Asn Pro Pro Pro
225                 230                 235                 240

Ile Gly Ser Val Ile Thr Tyr Lys Tyr Arg Gly Ile Thr Asn Ser Gly
                245                 250                 255

Lys Pro Arg Phe Ala Thr Tyr Trp Arg Glu Lys Lys
            260                 265

<210> SEQ ID NO 6
<211> LENGTH: 268
<212> TYPE: PRT
<213> ORGANISM: Haemophilus influenzae

<400> SEQUENCE: 6

Met Lys Phe Tyr Arg Thr Leu Leu Leu Phe Ala Ser Ser Phe Ala
1               5                   10                  15

Phe Ala Asn Ser Asp Leu Met Leu Leu His Thr Tyr Asn Asn Gln Pro
            20                  25                  30

Ile Glu Gly Trp Val Met Ser Glu Lys Leu Asp Gly Val Arg Gly Tyr
        35                  40                  45

Trp Asn Gly Lys Gln Leu Leu Thr Arg Gln Gly Gln Arg Leu Ser Pro
    50                  55                  60

Pro Ala Tyr Phe Ile Lys Asp Phe Pro Pro Phe Ala Ile Asp Gly Glu
65                  70                  75                  80

Leu Phe Ser Glu Arg Asn His Phe Glu Glu Ile Ser Ser Ile Thr Lys
                85                  90                  95

Ser Phe Lys Gly Asp Gly Trp Glu Lys Leu Lys Leu Tyr Val Phe Asp
            100                 105                 110

Val Pro Asp Ala Glu Gly Asn Leu Phe Glu Arg Leu Ala Lys Leu Lys
        115                 120                 125

Ala His Leu Leu Glu His Pro Thr Thr Tyr Ile Glu Ile Ile Glu Gln
    130                 135                 140

Ile Pro Val Lys Asp Lys Thr His Leu Tyr Gln Phe Leu Ala Gln Val
145                 150                 155                 160

Glu Asn Leu Gln Gly Glu Gly Val Val Val Arg Asn Pro Asn Ala Pro
                165                 170                 175

Tyr Glu Arg Lys Arg Ser Ser Gln Ile Leu Lys Leu Lys Thr Ala Arg
            180                 185                 190

Gly Glu Glu Cys Thr Val Ile Ala His His Lys Gly Lys Gly Gln Phe
        195                 200                 205

Glu Asn Val Met Gly Ala Leu Thr Cys Lys Asn His Arg Gly Glu Phe
    210                 215                 220

Lys Ile Gly Ser Gly Phe Asn Leu Asn Glu Arg Glu Asn Pro Pro Pro
225                 230                 235                 240

Ile Gly Ser Val Ile Thr Tyr Lys Tyr Arg Gly Ile Thr Asn Ser Gly
                245                 250                 255

Lys Pro Arg Phe Ala Thr Tyr Trp Arg Glu Lys Lys
            260                 265

<210> SEQ ID NO 7
<211> LENGTH: 268
<212> TYPE: PRT
<213> ORGANISM: Haemophilus influenzae
```

<400> SEQUENCE: 7

```
Met Lys Phe Tyr Arg Thr Leu Leu Phe Ala Ser Ser Phe Ala
1               5                   10                  15

Phe Ala Asn Ser Asp Leu Met Leu Leu His Thr Tyr Asn Asn Gln Pro
            20                  25                  30

Ile Glu Gly Trp Val Met Ser Glu Lys Leu Asp Gly Val Arg Gly Tyr
        35                  40                  45

Trp Asn Gly Lys Gln Leu Leu Thr Arg Gln Gly Gln Arg Leu Ser Pro
    50                  55                  60

Pro Ala Tyr Phe Ile Lys Asp Phe Pro Pro Phe Ala Ile Asp Gly Glu
65                  70                  75                  80

Leu Phe Ser Glu Arg Asn His Phe Glu Glu Ile Ser Ser Ile Thr Lys
                85                  90                  95

Ser Phe Lys Gly Asp Gly Trp Glu Lys Leu Lys Leu Tyr Val Phe Asp
            100                 105                 110

Val Pro Asp Ala Glu Gly Asn Leu Phe Glu Arg Leu Ala Lys Leu Lys
        115                 120                 125

Ala His Leu Leu Glu His Pro Thr Thr Tyr Ile Glu Ile Glu Gln
    130                 135                 140

Ile Pro Val Lys Asp Lys Thr His Leu Tyr Gln Phe Leu Ala Gln Val
145                 150                 155                 160

Glu Asn Leu Gln Gly Glu Gly Val Val Val Arg Asn Pro Asn Ala Pro
                165                 170                 175

Tyr Glu Arg Lys Arg Ser Ser Gln Ile Leu Lys Leu Lys Thr Ala Arg
            180                 185                 190

Asp Glu Glu Cys Thr Val Ile Ala His His Lys Gly Lys Gly Gln Phe
        195                 200                 205

Glu Asn Val Met Gly Ala Leu Thr Cys Lys Asn His Arg Gly Glu Phe
    210                 215                 220

Lys Ile Gly Ser Gly Phe Asn Leu Asn Glu Arg Glu Asn Pro Pro
225                 230                 235                 240

Ile Gly Ser Val Ile Thr Tyr Lys Tyr Arg Gly Ile Thr Asn Ser Gly
                245                 250                 255

Lys Pro Arg Phe Ala Thr Tyr Trp Arg Glu Lys Lys
            260                 265
```

<210> SEQ ID NO 8
<211> LENGTH: 246
<212> TYPE: PRT
<213> ORGANISM: Haemophilus influenzae

<400> SEQUENCE: 8

```
Met Leu Leu His Thr Tyr Asn Asn Gln Pro Ile Glu Gly Trp Val Met
1               5                   10                  15

Ser Glu Lys Leu Asp Gly Val Arg Gly Tyr Trp Asn Gly Lys Gln Leu
            20                  25                  30

Leu Thr Arg Gln Gly Gln Arg Leu Ser Pro Pro Ala Tyr Phe Ile Lys
        35                  40                  45

Asp Phe Pro Pro Phe Ala Ile Asp Gly Glu Leu Phe Ser Glu Arg Asn
    50                  55                  60

His Phe Glu Glu Ile Ser Ser Ile Thr Lys Ser Phe Lys Gly Asp Gly
65                  70                  75                  80

Trp Glu Lys Leu Lys Leu Tyr Val Phe Asp Val Pro Asp Ala Glu Gly
                85                  90                  95
```

```
                Asn Leu Phe Glu Arg Leu Ala Lys Leu Lys Ala His Leu Leu Glu His
                            100                 105                 110

Pro Thr Thr Tyr Ile Glu Ile Ile Glu Gln Ile Pro Val Lys Asp Lys
                        115                 120                 125

Thr His Leu Tyr Gln Phe Leu Ala Gln Val Glu Asn Leu Gln Gly Glu
                        130                 135                 140

Gly Val Val Val Arg Asn Pro Asn Ala Pro Tyr Glu Arg Lys Arg Ser
                145                 150                 155                 160

Ser Gln Ile Leu Lys Leu Lys Thr Ala Arg Asp Glu Glu Cys Thr Val
                            165                 170                 175

Ile Ala His His Lys Gly Lys Gly Gln Phe Glu Asn Val Met Gly Ala
                            180                 185                 190

Leu Thr Cys Lys Asn His Arg Gly Glu Phe Lys Ile Gly Ser Gly Phe
                        195                 200                 205

Asn Leu Asn Glu Arg Glu Asn Pro Pro Ile Gly Ser Val Ile Thr
                        210                 215                 220

Tyr Lys Tyr Arg Gly Ile Thr Asn Ser Gly Lys Pro Arg Phe Ala Thr
                225                 230                 235                 240

Tyr Trp Arg Glu Lys Lys
                            245
```

ENHANCED LIGATION REACTIONS

CROSS REFERENCE TO RELATED APPLICATIONS

This subject application is a Continuation Application of U.S. application Ser. No. 15/071,086, filed Mar. 15, 2016, now U.S. Pat. No. 9,765,388, which is a Continuation Application of U.S. application Ser. No. 14/360,892, filed May 27, 2014, now U.S. Pat. No. 9,315,861, which is a U.S. National Application filed under 35 U.S.C. § 371 of International Application No. PCT/US2012/066869, filed on Nov. 28, 2012, which claims the benefit of priority under 35 U.S.C. § 119 to U.S. Provisional Application No. 61/564,243, filed on Nov. 28, 2011; and U.S. application Ser. No. 14/360,892, filed May 27, 2014 is a Continuation Application of U.S. application Ser. No. 13/980,280, filed on Oct. 1, 2013, which is a U.S. National Application filed under 35 U.S.C. § 371 of International Application No. PCT/US2012/021465, filed Jan. 17, 2012, which claims the benefit of priority under 35 U.S.C. § 119 to U.S. Provisional Application Nos. U.S. 61/433,488, filed on Jan. 17, 2011, U.S. 61/433,502, filed on Jan. 17, 2011, U.S. 61/474,168, filed on Apr. 11, 2011, and U.S. 61/474,205, filed on Apr. 11, 2011, the disclosures of which are incorporated herein by reference in their entireties.

Throughout this application various publications, patents, and/or patent applications are referenced. The disclosures of these publications, patents, and/or patent applications in their entireties are hereby incorporated by reference into this application in order to more fully describe the state of the art to which this invention pertains.

The instant application contains a Sequence Listing which is submitted herewith in ASCII format via EFS-Web and is hereby incorporated by reference in its entirety. Said ASCII copy, created on Nov. 14, 2012, is named LT00621PCT_Sequence_Listing_ST25.txt, and is 20 kilobytes in size.

FIELD

Enhancement of nucleic acid ligation efficiency comprises an enzyme that resolves abortive ligation intermediates.

INTRODUCTION

DNA ligases join together nucleic acid ends by forming a phosphodiester bond at single-stranded or double-stranded breaks in a DNA duplex. Generally, a mechanism for DNA ligases involves production of an adenylated intermediate that can fail to undergo formation of a phosphodiester bond to join the ends. Production of these adenylated intermediates can reduce ligation efficiency.

SUMMARY

In some embodiments, the present teachings provide compositions, systems, methods and kits for ligation of two nucleic acid ends. Nucleic acid ligation includes joining together two nucleic acid ends. Methods for nucleic acid ligation comprise two or more enzymes. In some embodiments, a ligation reaction can include two or more enzymatic reactions. In some embodiments, an enzymatic reaction includes forming a phosphodiester bond between two nucleic acid ends. A reaction catalyzed by a first enzyme can sometimes produce intermediates that fail to join. In some embodiments, a second enzymatic reaction includes resolving the failed intermediates to produce termini that undergo successful ligation.

In some embodiments, the present teachings provide a method for nucleic acid ligation comprising: conducting a nucleic acid ligation reaction in the presence of one or more agents that catalyze removal of an adenylate group from a terminal 5' phosphate of a nucleic acid.

Optionally, methods for nucleic acid ligation comprise: conducting a nucleic acid ligation reaction in the presence of at least one agent that generates a ligatable terminal 5' phosphate group by removing an adenylate group from a terminal 5' phosphate of a nucleic acid.

Optionally, methods for nucleic acid ligation comprise: conducting a nucleic acid ligation reaction in the presence of an aprataxin enzyme under conditions suitable for ligating nucleic acids together.

Optionally, methods for nucleic acid ligation comprise a ligase enzyme.

Optionally, methods for nucleic acid ligation comprise two nucleic acid ends.

Optionally, methods for nucleic acid ligation comprise: contacting two nucleic acid ends with at least one ligase enzyme and at least one aprataxin enzyme under conditions suitable for ligating nucleic acid ends Optionally, methods for nucleic acid ligation comprise: contacting an adenylated nucleic acid with an aprataxin enzyme under conditions suitable for ligating nucleic acid ends and suitable for aprataxin activity.

Optionally, methods for nucleic acid ligation comprise: closing a single-stranded nick on a nucleic acid duplex. In some embodiments, the nick is formed by a first and second oligonucleotide hybridized to a polynucleotide, wherein the first and second oligonucleotides abut each other.

Optionally, the nucleic acid ligation reaction comprises: joining together two ends of two nucleic acids. In some embodiments, at least one end of one of the nucleic acids is attached to a surface. In some embodiments, the surface comprises a planar surface, bead or particle.

Optionally, the nucleic acid ligation reaction comprises: joining together two ends of a single nucleic acid to circularize the single nucleic acid.

In some embodiments, the present teachings provide a method for nucleic acid ligation comprising: conducting at least one cycle of a repetitive cycle ligation reaction in the presence of an aprataxin enzyme under conditions suitable for ligating nucleic acid ends. In some embodiments, the repetitive cycle ligation reaction comprises: a ligase chain reaction (LCR), gap LCR, or ligation detection reaction (LDR).

Optionally, the aprataxin enzyme comprises an amino acid sequence according to SEQ ID NO:1.

Optionally, the ligase comprises a mesophilic or thermostable ligase enzyme. In some embodiments, the ligase comprises an *E. coli* DNA ligase, Taq DNA ligase, 9° N DNA ligase, or T4 DNA ligase.

Optionally, the ligase comprises a small footprint ligase enzyme. In some embodiments, the small footprint ligase joins together a polynucleotide to an oligonucleotide comprising 8, 7, 6, 5, 4, 3 or 2 nucleotides in length. In some embodiments, the small footprint ligase comprises an amino acid sequence of any one of SEQ ID NOS:3-8.

In some embodiments, the present teachings provide a method for joining together a plurality of unbound nucleic acids to a plurality of immobilized nucleic acids, comprising: contacting the plurality of unbound nucleic acids and the plurality of immobilized nucleic acids with at least one ligase enzyme and at least one aprataxin enzyme under conditions suitable for nucleic acid ligation. In some embodiments, one end of the plurality of immobilized nucleic acids is attached to a surface. In some embodiments, the surface comprises a planar surface, a bead or a particle. In some embodiments, the plurality of immobilized nucleic acids joined to the plurality of unbound nucleic acids is subjected to a sequencing reaction.

In some embodiments, the present teachings provide a method for preparing a nucleic acid-templated surface, comprising: contacting (i) a plurality of nucleic acids that are attached to a surface (e.g., immobilized) and (ii) a plurality of unbound nucleic acids with at least one ligase enzyme and at least one aprataxin enzyme under conditions suitable for nucleic acid ligation thereby generating a plurality of templated nucleic acids. In some embodiments, the method further comprises sequencing the plurality of templated nucleic acids. In some embodiments, the plurality of immobilized nucleic acids joined to the plurality of unbound nucleic acids is subjected to a sequencing reaction.

In some embodiments, the present teachings provide a method for sequencing comprising: (a) hybridizing a template polynucleotide to a first and second oligonucleotide probe so that the first and second oligonucleotide probes abut each other to form a nick; (b) contacting the nick with at least one aprataxin enzyme and at least one ligase enzyme to close the nick; and (c) detecting the distinctive detectable reporter moiety so as to determine the sequence of the first or second oligonucleotide probe hybridized to the template polynucleotide. Optionally, the first or second oligonucleotide probe can be labeled with a distinctive detectable reporter moiety. Optionally, the template polynucleotide can be attached to a surface. Optionally, the aprataxin enzyme comprises an amino acid sequence according to SEQ ID NO:1. Optionally, the ligase comprises a small footprint ligase having an amino acid sequence according to any one of SEQ ID NOS:3-8.

In some embodiments, the present teaching provide a method for sequencing comprising: (a) hybridizing a template polynucleotide to a first and second oligonucleotide probe so that the first and second oligonucleotide probes abut each other to form a first nick, wherein the second oligonucleotide probe is labeled with a first distinctive detectable reporter moiety; (b) contacting the first nick with at least one aprataxin enzyme and at least one ligase enzyme to close the first nick (e.g., join together the first and second oligonucleotide probes); (c) detecting the first distinctive detectable reporter moiety thereby determining the sequence of the second oligonucleotide probe hybridized to the template polynucleotide; (d) hybridizing the template polynucleotide to a third oligonucleotide probe so that the third and second oligonucleotide probes abut each other to form a second nick, wherein the third oligonucleotide probe is labeled with a second distinctive detectable reporter moiety; (e) contacting the second nick with at least one aprataxin enzyme and at least one ligase enzyme to close the second nick; and (f) detecting the second distinctive detectable reporter moiety thereby determining the sequence of the third oligonucleotide probe hybridized to the template polynucleotide. Optionally, the template polynucleotide can be attached to a surface.

In some embodiments, the present teaching provide a method for sequencing comprising: (a) hybridizing a template polynucleotide to a first and second oligonucleotide probe so that the first and second oligonucleotide probes abut each other to form a first nick, wherein the second oligonucleotide probe is labeled with a first distinctive detectable reporter moiety; (b) contacting the first nick with at least one aprataxin enzyme and at least one ligase enzyme to close the first nick (e.g., join together the first and second oligonucleotide probes); (c) detecting the first distinctive detectable reporter moiety thereby determining the sequence of the second oligonucleotide probe hybridized to the template polynucleotide; (d) hybridizing the template polynucleotide to a third and fourth oligonucleotide probe so that the third and fourth oligonucleotide probes abut each other to form a second nick, wherein the fourth oligonucleotide probe is labeled with a second distinctive detectable reporter moiety; (e) contacting the second nick with at least one aprataxin enzyme and at least one ligase enzyme to close the second nick; and (f) detecting the second distinctive detectable reporter moiety thereby determining the sequence of the fourth oligonucleotide probe hybridized to the template polynucleotide. Optionally, the template polynucleotide can be attached to a surface.

In some embodiments, the present teachings provide a composition comprising two nucleic acid ends ligated together according to the methods for nucleic acid ligation disclosed herein.

In some embodiments, the present teachings provide a composition comprising a first and second oligonucleotide hybridized to a polynucleotide and ligated together according to the methods for nucleic acid ligation disclosed herein.

In some embodiments, the present teachings provide a composition comprising two ends of two nucleic acids ligated together according to according to the methods for nucleic acid ligation disclosed herein.

In some embodiments, the present teachings provide a composition comprising two ends of a single nucleic acid joined together according to the methods for nucleic acid ligation disclosed herein.

In some embodiments, the present teachings provide a composition comprising a product of at least one cycle of a repetitive cycle ligation reaction generated according to the methods for nucleic acid ligation disclosed herein.

In some embodiments, the present teachings provide a composition comprising a plurality of unbound nucleic acids ligated to a plurality of immobilized nucleic acids according to the methods for nucleic acid ligation disclosed herein.

In some embodiments, the present teachings provide an isolated aprataxin enzyme comprises an amino acid sequence according to SEQ ID NO:1.

In some embodiments, the present teachings provide a small footprint ligase comprises an amino acid sequence of any one of SEQ ID NOS:3-8.

DRAWINGS

FIG. 2A is a non-limiting embodiment of an amino acid sequence of a human aprataxin enzyme (SEQ ID NO:1).

FIG. 2B is a non-limiting embodiment of a nucleotide sequence of a human aprataxin enzyme (SEQ ID NO:2).

FIG. 3 is a non-limiting embodiment of an amino acid sequence of a ligase from *Paramecium bursaria Chlorella* virus (SEQ ID NO:3).

FIG. 4 is a non-limiting embodiment of an amino acid sequence of a ligase from *Burkholderia pseudomallei* (SEQ ID NO:4).

FIG. 5 is a non-limiting embodiment of an amino acid sequence of a ligase from *Haemophilus* influenza (SEQ ID NO:5).

FIG. 6 is a non-limiting embodiment of an amino acid sequence of an artificial ligase derived from *Haemophilus influenza* (SEQ ID NO:6).

FIG. 7 is a non-limiting embodiment of an amino acid sequence of an artificial ligase derived from *Haemophilus influenza* (SEQ ID NO:7).

FIG. 8 is a non-limiting embodiment of an amino acid sequence of a ligase from *Haemophilus influenza* (SEQ ID NO:8).

Figure 1:
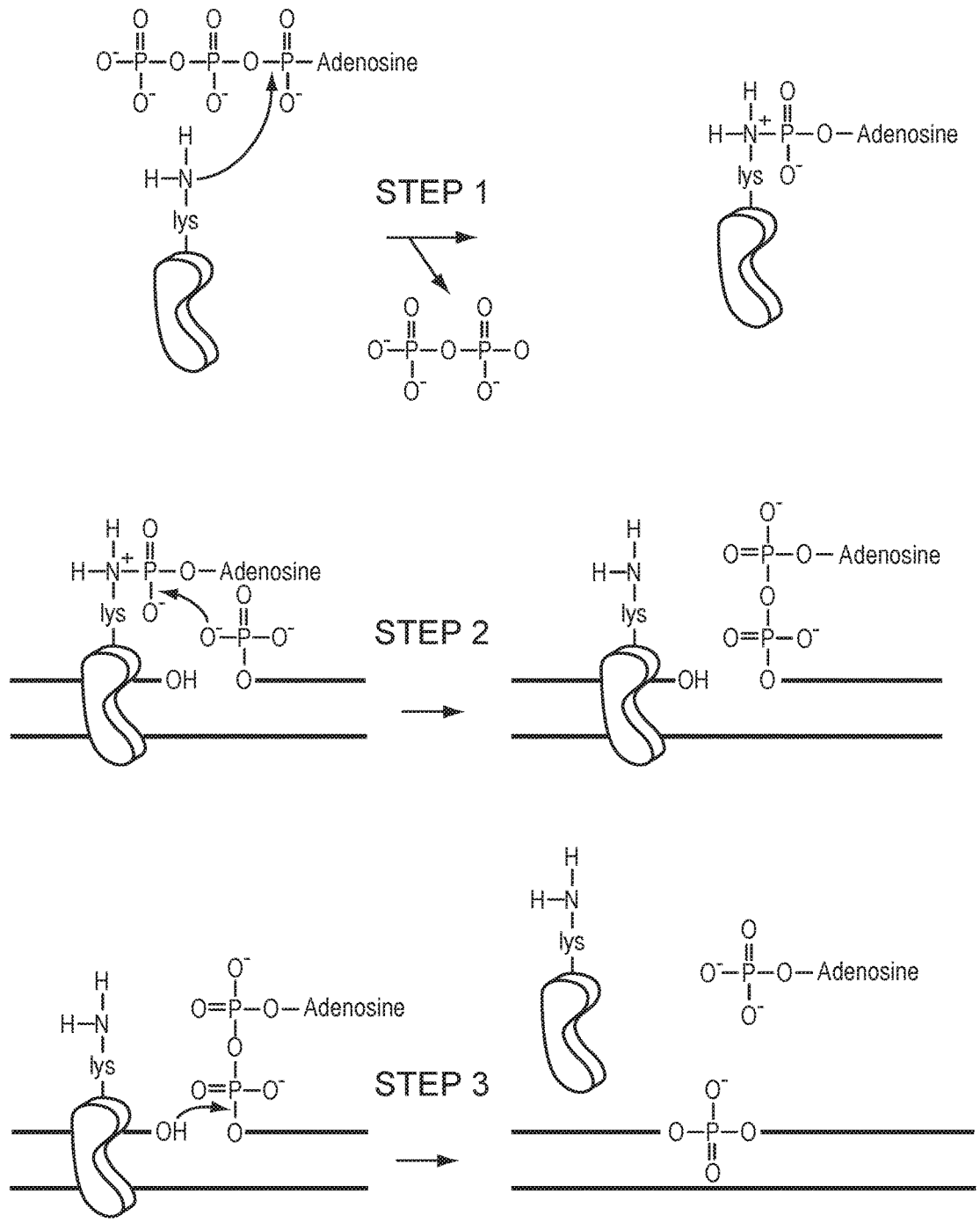
FIG. 1 is a schematic depicting non-limiting embodiments of a general mechanism for DNA ligation.

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition and/or description is set forth herein that is contrary to or otherwise inconsistent with any definition set forth in the patents, patent applications, published applications, and other publications that are herein incorporated by reference, the definition and/or description set forth herein prevails over the definition that is incorporated by reference. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present). It is to be understood that both the foregoing general description and the following detailed description are exemplary and explanatory only and are not restrictive of the invention.

DEFINITIONS

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques described herein are those well known and commonly used in the art.

As utilized in accordance with exemplary embodiments provided herein, the following terms, unless otherwise indicated, shall be understood to have the following meanings:

As used herein the terms "ligate" and "ligation" refer to joining together two free nucleic acid ends by forming a phosphodiester bond between the two free ends. In some embodiments, ligation can include joining together two ends of two nucleic acid strands or joining together two ends of a single nucleic acid strand (e.g., circularization). Ligation can include joining together two ends of two single-stranded nucleic acids or joining together two ends two double-stranded nucleic acids. Ligation can include closing a single-stranded nick in a nucleic acid duplex.

As used herein the term "nick" refers to a location on a double-stranded nucleic acid that lacks a phosphodiester bond between adjacent nucleotides of one of the nucleic acid strands, while the other strand has adjacent nucleotides joined by a phosphodiester bond at that same location. In some embodiments, a phosphodiester bond includes analog linkages that join adjacent nucleotides (or nucleotide analogs).

As used herein the term "adenylated nucleic acid" and "adenylated DNA" refers to an adenylate group that is covalently linked to a nucleic acid. For example, an "adenylated nucleic acid" comprises an adenylate group that is covalently linked to a terminal 5'-phosphate of a nucleic acid or an adenosine-5'-phosphate linked to a terminal 5'-phosphate of a nucleic acid.

As used herein the terms "nucleic acids", "oligonucleotides" and "polynucleotides" refers to single-stranded or double-stranded nucleic acids, and includes DNA, RNA, chimeric RNA/DNA, and derivatives thereof.

DESCRIPTION OF VARIOUS EMBODIMENTS

In some embodiments, the present teachings provide compositions, systems, methods and kits for enhanced ligation of two nucleic acid ends.

A general mechanism for DNA ligation involves several steps, including but not limited to: (1) a ligase enzyme reacts with ATP to form an enzyme-adenylate complex (with an activated AMP) and releases ADP; (2) the enzyme-adenylate complex transfers the activated AMP to a 5'-terminal phosphate of a nucleic acid to form an adenylated DNA strand; and (3) the enzyme catalyzes formation of a phosphodiester bond between the adenylated DNA and a terminal 3'OH end of a nucleic acid to join together the two nucleic acid ends and release of AMP (FIG. 1).

An abortive ligation reaction can result from formation of adenylated DNA intermediates and failure to proceed to formation of phosphodiester bonds. Abortive ligation reactions can reduce ligation reaction efficiency. Aborted ligation reactions can be rescued by reversing the adenylation step to restore DNA molecules having a terminal 5' phosphate group which can proceed to adenylation and phosphodiester bond formation.

Aprataxin enzyme can reverse the DNA adenylation reaction to produce a nucleic acid having a ligatable end. Aprataxin can resolve aborted DNA ligation intermediates by catalyzing nucleophilic release of adenylate groups that are linked to a terminal 5'-phosphate group to regenerate a terminal 5'-phosphate group that can be joined via phosphodiester bond formation (Ahel 2006 Nature 443:713-716).

In some embodiments, compositions, systems, methods and kits for enhancing ligation of nucleic acids comprise ligase and aprataxin enzymes. Aprataxin can enhance a ligation reaction by improving the efficiency of a nucleic acid ligation reaction. Aprataxin can improve the number-fold and/or rate of nucleic acid ligation by resolving aborted adenylated ligation intermediates.

In some embodiments, methods for enhancing a nucleic acid ligation reaction comprise joining together two nucleic acid ends. In some embodiments, methods for enhancing a nucleic acid ligation reaction comprise closing a single-stranded nick on a nucleic acid duplex or joining together two ends of two nucleic acids or joining together two ends of a single nucleic acid (e.g., circularization).

In some embodiments, methods for enhancing a nucleic acid ligation reaction comprise: conducting a nucleic acid ligation reaction in the presence of one or more agents that catalyze removal of an adenylate group from a terminal 5' phosphate of a nucleic acid. In some embodiments, methods for enhancing a nucleic acid ligation reaction comprise: conducting a nucleic acid ligation reaction in the presence of at least one agent that generates a ligatable terminal 5' phosphate group by removing an adenylate group from a terminal 5' phosphate of a nucleic acid. In some embodiments, an aprataxin enzyme can catalyze removal of an adenylate group from a terminal 5' phosphate of a nucleic acid.

In some embodiments, methods for joining together two nucleic acid ends comprises: conducting a nucleic acid ligation reaction in the presence of one or more agents that catalyze removal of an adenylate group from a terminal 5' phosphate of a nucleic acid. In some embodiments, methods for joining together two nucleic acid ends comprises: conducting a nucleic acid ligation reaction in the presence of at least one agent that generates a ligatable terminal 5' phosphate group by removing an adenylate group from a terminal 5' phosphate of a nucleic acid. In some embodiments, an aprataxin enzyme can catalyze removal of an adenylate group from a terminal 5' phosphate of a nucleic acid.

In some embodiments, a ligation reaction comprises forming a phosphodiester bond between the termini of two nucleic acid ends. In some embodiments, a ligation reaction comprises forming a phosphodiester bond between a 5' terminus of a first nucleic acid end and a 3' terminus of a second nucleic acid end.

In some embodiments, methods for enhancing a nucleic acid ligation reaction comprise: conducting a nucleic acid ligation reaction in the presence of an aprataxin enzyme under conditions suitable for ligating nucleic acid ends.

In some embodiments, methods for enhancing a nucleic acid ligation reaction comprise: contacting two nucleic acid ends with at least one ligase enzyme and at least one aprataxin enzyme under conditions suitable for ligating nucleic acid ends.

In some embodiments, methods for enhancing a nucleic acid ligation reaction comprise: conducting at least one cycle of a repetitive cycle ligation reaction in the presence of an aprataxin enzyme under conditions suitable for ligating nucleic acid ends.

In some embodiments, methods for enhancing a nucleic acid ligation reaction comprise: contacting a ligase enzyme and an aprataxin enzyme with (i) a single-stranded nick on a nucleic acid duplex or (ii) two double-stranded nucleic acids or (iii) two single-stranded nucleic acids, under conditions suitable for ligating nucleic acid ends.

In some embodiments, methods for enhancing a nucleic acid ligation reaction comprise: contacting an adenylated nucleic acid with an aprataxin enzyme under conditions suitable for ligating nucleic acid ends (e.g., ligation reaction) and suitable for aprataxin activity.

In some embodiments, methods for enhancing a nucleic acid ligation reaction comprise: contacting in any order and in any combination an adenylated nucleic acid, a ligase enzyme and an aprataxin enzyme, under conditions suitable for ligating nucleic acid ends and suitable for aprataxin activity.

In some embodiments, methods for enhancing a nucleic acid ligation reaction comprise: contacting an adenylated nucleic acid simultaneously (e.g., essentially simultaneously) or sequentially with a ligase enzyme and an aprataxin enzyme.

In some embodiments, methods for enhancing a nucleic acid ligation reaction comprise: contacting two nucleic acid ends with a ligase enzyme and an aprataxin enzyme in the same or different reaction vessels.

In some embodiments, a ligation reaction comprises joining together nucleic acid ends, where at least one end of a nucleic acid can be attached to a surface (e.g., immobilized). For example, a nucleic acid end that will not be joined to another nucleic acid end can be attached to a surface.

In some embodiments, methods for enhancing a nucleic acid ligation reaction include conducting a nucleic acid ligation reaction in the presence of an aprataxin enzyme to increase the number of ligated nucleic acid products compared to the number of ligated nucleic acid products resulting from a ligation reaction lacking an aprataxin enzyme. For example, an increase in the number of ligated nucleic acid products can range from about 1-5%, or about 10-20%, or about 20-30%, or about 30-40%, or about 40-50%, or a higher percentage increase in formation of ligation products.

In some embodiments, a suitable nucleic acid ligation condition includes well known parameters, such as: time, temperature, pH, buffers, reagents, cations, salts, co-factors, nucleotides, nucleic acids, and enzymes. In some embodiments, a nucleic acid ligation reaction can be conducted with a reagent that includes ATP and/or NAD. In some embodiments, a reagent or buffer can include a source of ions, such as KCl, K-acetate, $NH_4$-acetate, K-glutamate, $NH_4Cl$, or ammonium sulfate. In some embodiments, a reagent or buffer can include a source of ions, such as magnesium, manganese, cobalt, or calcium. In some embodiments, a reagent or buffer can include acetate or chloride. In some embodiments, a buffer can include Tris, Tricine, HEPES, MOPS, ACES, MES, or inorganic buffers such as phosphate or acetate-based buffers which can provide a pH range of about 4-12. In some embodiments, a buffer can include chelating agents such as EDTA or EGTA. In some embodiments, a buffer can include dithiothreitol (DTT), glycerol, spermidine, BSA (bovine serum albumin) and/or Tween.

In some embodiments, a suitable condition includes conducting a nucleic acid ligation reaction for a time, such as about 1-10 seconds, or about 10-60 seconds, or about 1-30 minutes, or about 30-60 minutes, or about 1-3 hours, or about 3-6 hours, or about 6-12 hours, or about 12-24 hours, or longer.

In some embodiments, a suitable condition includes conducting a nucleic acid ligation reaction under thermo-cycle conditions, or isothermal temperature conditions, or a combination of both. In some embodiments, a suitable condition includes conducting a nucleic acid ligation reaction at a temperature range of about 0-10° C., or about 10-20° C., or about 20-30° C., or about 30-40° C., or about 40-50° C., or about 50-60° C., or about 60-70° C., or about 70-80° C., or about 80-90° C., or about 90-99° C., or a higher temperature range.

In some embodiments, a suitable condition includes conducting a nucleic acid ligation reaction at a pH range of about 5-9, or a pH range of about 6-8, or a pH range of about 7-7.5.

In some embodiments, a suitable condition includes conducting a nucleic acid ligation reaction in a tube, well or flowcell. In some embodiments, the well can be a part of an array or a multi-well plate or a multi-well chip.

In some embodiments, a ligation reaction comprises closing a single-stranded nick on a nucleic acid duplex. For example, a first and second oligonucleotide can be hybridized to a polynucleotide. The first and second oligonucleotides can abut each other, while hybridized to the polynucleotide, to create a nick. In some embodiments, methods for closing a nick comprise contacting two nucleic acid ends that form the nick with a ligase and aprataxin enzyme.

In some embodiments, a first or second oligonucleotide or the polynucleotide can be labeled with a detectable reporter moiety (e.g., a fluorophore, luminophore, chemiluminophore, or bioluminophore). In some embodiments, a first or second oligonucleotide or the polynucleotide can be attached to a solid surface. In some embodiments, a first or second oligonucleotide or the polynucleotide can include an internal or terminal scissile linkage such as a phosphoramidate, phosphorothioate, or phosphorodithiolate linkage.

In some embodiments, the polynucleotide can comprise a single-stranded nucleic acid template, and the first and second oligonucleotides can comprise labeled or non-labeled oligonucleotide probes. In some embodiments, the first or second oligonucleotide probes comprise 4-500 nucleotides in length or longer. In some embodiments, the first and second oligonucleotide probes abut each other while hybridized to the polynucleotide template. In some embodiments, the first and second oligonucleotide probes comprise nucleotide sequences that are complementary to at least a portion of the polynucleotide template. In some embodiments, hybridization of the first and second oligonucleotide probes to the polynucleotide template forms a nick. In some embodiments, closing the nick by ligation with a ligase in the presence of an aprataxin can increase ligation efficiency. In some embodiments, hybridizing first and second oligonucleotide probes to a polynucleotide template to form a nick, and closing the nick with a ligase reaction in the presence of an aprataxin enzyme can be used for determining the sequence of the polynucleotide template. In some embodiments, the hybridization and/or closing-the-nick steps can be conducted under isothermal or thermo-cyclic conditions. In some embodiments, the ligase and/or aprataxin can be a mesophilic or thermostable enzyme. In some embodiments, aprataxin can be used to enhance ligation reactions as conducted in a SOLiD sequencing reaction (WO 2006/084132) by Applied Biosystems (now part of Life Technologies, Carlsbad, Calif.).

In some embodiments, a method for sequencing comprises: (a) hybridizing a template polynucleotide to a first and second oligonucleotide probe so that the first and second oligonucleotide probes abut each other when hybridized to the polynucleotide to form a nick, wherein the first or second oligonucleotide probe is labeled with a distinctive detectable reporter moiety; (b) contacting the nick with at least one aprataxin enzyme and at least one ligase enzyme to close the nick (e.g., join together the first and second oligonucleotide probes); and (c) detecting the distinctive detectable reporter moiety so as to determine the sequence of the first or second oligonucleotide probe hybridized to the template polynucleotide. In some embodiments, steps (a)-(c) can be repeated, for example by hybridizing the template polynucleotide to a third oligonucleotide probe so that the third and second oligonucleotide probes abut each other when hybridized to the polynucleotide to form a second nick, wherein the third oligonucleotide probe is labeled with a second distinctive detectable reporter moiety; (b) contacting the second nick with at least one aprataxin enzyme and at least one ligase enzyme to close the second nick; and (c) detecting the second distinctive detectable reporter moiety so as to determine the sequence of the third oligonucleotide probe hybridized to the template polynucleotide. In some embodiments, first, second and third oligonucleotide probes can have different sequences. In some embodiments, first, second and third oligonucleotide probes can be labeled with different or distinct detectable reporter moieties to distinguish the different sequences of the probes. In some embodiments, methods for sequencing comprise a SOLiD sequencing reaction (WO 2006/084132). In some embodiments, steps (a)-(c) can be repeated, for example by hybridizing the template polynucleotide to a third and forth oligonucleotide probe so that the third and fourth oligonucleotide probes abut each other when hybridized to the polynucleotide to form a second nick, wherein the third or fourth oligonucleotide probe is labeled with a second distinctive detectable reporter moiety; (b) contacting the second nick with at least one aprataxin enzyme and at least one ligase enzyme to close the second nick; and (c) detecting the second distinctive detectable reporter moiety so as to determine the sequence of the third or fourth oligonucleotide probe hybridized to the template polynucleotide. In some embodiments, first, second, third and fourth oligonucleotide probes can have different sequences. In some embodiments, first, second, third and fourth oligonucleotide probes can be labeled with different or distinct detectable reporter moieties to distinguish the different sequences of the probes. In some embodiments, methods for sequencing comprise a SOLiD sequencing reaction (WO 2006/084132).

In some embodiments, methods for closing a nick comprise: contacting a nick with a small footprint ligase and an aprataxin enzyme under conditions suitable for ligase activity. Non-limiting examples of small footprint ligases are shown in FIGS. 3-8 (SEQ ID NOS: 3-8). A non-limiting example of aprataxin is shown in FIG. 2A (SEQ ID NO: 1).

In some embodiments, a ligation reaction comprises joining together two ends of two nucleic acids with a ligase and aprataxin enzyme. In some embodiments, the two nucleic acids comprise single- or double-stranded nucleic acids. In some embodiments, a ligation reaction comprises joining together two blunt ends or two overhang ends. For example, a ligation reaction comprises joining together a first end of a first nucleic acid with a first end of a second nucleic acid. In some embodiments, a first and/or second nucleic acid can be any combination of a nucleic acid adaptor, polynucleotide-of-interest, target sequence, template, insert sequence, fragment library construct and/or mate pair library construct. In some embodiments, a first or second nucleic acid can be unbound (non-immobilized) or can be immobilized.

In some embodiments, a ligation reaction comprises joining together a plurality of unbound nucleic acids to a plurality of immobilized nucleic acids with a ligase and aprataxin enzyme. In some embodiments, joining together a plurality of unbound nucleic acids to a plurality of immobilized nucleic acids comprises contacting the plurality of unbound nucleic acids and the plurality of immobilized nucleic acids with at least one ligase enzyme and at least one aprataxin enzyme.

In some embodiments, the plurality of unbound nucleic acids comprise un-amplified nucleic acids, or comprise nucleic acids resulting from an amplification reaction. In some embodiments, a linear amplification or exponent amplification reaction can generate a plurality of unbound nucleic acids. In some embodiments, a PCR or emPCR reaction can generate a plurality of unbound nucleic acids.

In some embodiments, a plurality of unbound nucleic acids can be in an aqueous solution, or can be in an aqueous compartment of an oil emulsion. In some embodiments, immobilized nucleic acids can be in an aqueous solution, or can be in an aqueous compartment of an oil emulsion. In some embodiments, the plurality of unbound nucleic acids and the immobilized nucleic acids reside in the same aqueous solution or the same aqueous compartment of an oil emulsion during amplification of the unbound nucleic acids. In some embodiments, the plurality of unbound nucleic acids and the immobilized nucleic acids reside in separate aqueous solutions or separate aqueous compartments of an oil emulsion during amplification of the unbound nucleic acids.

In some embodiments, joining together the plurality of unbound nucleic acids to the plurality of immobilized nucleic acids with a ligase and aprataxin enzyme can be conducted under isothermal or thermo-cyclic conditions. In some embodiments, the ligase and/or aprataxin can be a mesophilic or thermostable enzyme.

In some embodiments, the immobilized nucleic acids comprise nucleic acids attached to a surface (e.g., planar, bead or particle). In some embodiments, a plurality of unbound nucleic acids comprises a plurality of template nucleic acids. In some embodiments, joining together a plurality of unbound nucleic acids (e.g., templates) to a plurality of immobilized nucleic acids with a ligase and aprataxin enzyme generates one or more nucleic acid-templated surfaces (e.g., nucleic acids attached to a surface). In some embodiments, methods for preparing a nucleic acid-templated surface comprise: contacting at least one ligase enzyme and at least one aprataxin enzyme with (i) a plurality of nucleic acids that are attached to a surface and (ii) a plurality of unbound nucleic acids under conditions suitable for nucleic acid ligation. In some embodiments, nucleic acid-templated surfaces can be subjected to any next generation sequencing reaction. For example, sequencing reagents can be delivered to the nucleic acid-templated surfaces to conduct a sequencing reaction. In some embodiments, a sequencing reaction includes any next generation sequencing reaction, including: sequencing by oligonucleotide probe ligation and detection (e.g., SOLiD™ from Life Technologies, WO 2006/084131); probe-anchor ligation sequencing (e.g., Complete Genomics™ or Polonator™); sequencing-by-synthesis (e.g., Genetic Analyzer, HiSeq™ and MiSeg™ from Illumina); pyrophosphate sequencing (e.g., Genome Sequencer FLX from 454 Life Sciences); ion-sensitive sequencing (e.g., Personal Genome Machine from Ion Torrent™ Systems, Life Technologies); and single molecule sequencing platforms (e.g., HeliScope™ from Helicos). In some embodiments, a sequencing reaction comprises use of a chain-terminating nucleotide, including reversible chain-terminating nucleotides (U.S. Pat. No. 7,476,734, Liu; U.S. Pat. No. 7,713,698, Ju; U.S. Pat. No. 8,158,346; Balasubramanian; U.S. Pat. No. 7,771,973, Milton; U.S. Pat. No. 8,088,575, Ju; U.S. Pat. No. 7,414,116, Milton; U.S. Pat. No. 7,785,796, Balasubramanian; U.S. Pat. No. 7,345,159, Ju; U.S. Pat. No. 7,816,503, Milton; U.S. Pat. No. 7,713,68, Ju; U.S. Pat. No. 7,883,869, Ju; U.S. Pat. No. 7,541,444, Milton; U.S. Pat. Nos. 8,148,064 and 8,158,346, Balasubramanian; U.S. Pat. Nos. 7,713,698 and 7,790,869, Ju; U.S. Pat. No. 8,298,792, Ju; U.S. Pat. No. 7,771,973, Milton; U.S. Pat. No. 6,664,079, Ju; and U.S. Pat. No. 7,635,578, Ju).

In some embodiments, a ligation reaction comprises joining together two ends of a single nucleic acid. In some embodiments, a ligation reaction comprises a ligase and aprataxin enzyme to improve the number-fold and/or rate of nucleic acid ligation. In some embodiments, the single nucleic acid comprises a single- or double-stranded nucleic acid. In some embodiments, a ligation reaction comprises joining together two blunt ends or two overhang ends. For example, a ligation reaction comprises joining together a first and second end of a first nucleic acid.

In some embodiments, methods for enhancing a nucleic acid ligation reaction comprise conducting at least one cycle of a repetitive cycle ligation reaction with a ligase enzyme and an aprataxin enzyme. In some embodiments, the ligase enzyme can be a mesophilic or thermostable ligase enzyme.

In some embodiment, a repetitive cycle ligation reaction generally comprises three steps: (a) probe hybridization; (b) ligation; and (c) detection. In some embodiments, steps (a)-(c) can be repeated at least once. In some embodiments, a probe hybridization step comprises hybridizing a pair of oligonucleotide probes to a template/target polynucleotide such that the probes hybridize in close proximity to each (e.g., to form a nick or gap). In some embodiments, a ligation step comprises joining together a pair of hybridized oligonucleotide probes to generate ligated probe products. In some embodiments, ligation may be disrupted if the hybridized probes lack complementarity to the template/target polynucleotide. For example, probes having partial complementarity to the template/target polynucleotide may not be ligated together. In some embodiments, the detecting step comprises detecting the presence of the ligated probe products. In some embodiments, amplification of the ligated probe products can occur prior to, or subsequent to, a detection step.

Non-limiting examples of repetitive cycle ligation reactions include: ligase chain reaction (LCR, also known as oligonucleotide ligase amplification (OLA)); gap LCR; ligation detection reaction (LDR); combined chain reaction (CCR which includes a combination of PCR and LCR); and methods coupled with polymerase chain reaction (PCR), including OLA-PCR, PCR-OLA and PCR-LDR.

In some embodiments, a ligation chain reaction (LCR) comprises a nucleic acid amplification method in which two pairs of oligonucleotide probes hybridize at adjacent positions to complementary strands of a double-stranded target polynucleotide (Wu and Wallace 1989 Genomics 4:560; Barany 1991 PNAS 88:189-193; U.S. Pat. No. 5,185,243 to Ullman, U.S. Pat. No. 5,427,930 to Birkenmeyer, U.S. Pat. No. 5,573,907 to Carrino U.S. Pat. No. 5,679,524 to Nikiforov, U.S. Pat. No. 5,869,252 to Bouma, U.S. Pat. No. 6,858,412 to Willis; EP 0320308 to Backman, EP 0336731 to Wallace, EP 0439182 to Backman; and WO 1990/01069 to Segav, WO 1989/12696 to Richards, WO 1989/09835 to Orgel and WO 1996/015271 to Carrino). The hybridized oligonucleotide probes can be ligated together with ligase and aprataxin, then removed via denaturation. Multiple rounds of annealing, ligating and denaturing result in exponential amplification of the target polynucleotide. In some embodiments, one or both of the oligonucleotide probes can have substantially perfect complementarity or partial complementarity to the target polynucleotide.

In some embodiments, a modified LCR method comprises PCR reactions with limited LCR (Wiedmann 1992 Appl Environ. Microbiol. 58:3443-3447; Wiedmann 1993 Appl Environ. Microbiol. 59:2743-2745).

In some embodiments, a gap LCR reaction comprises hybridizing a target polynucleotide to a pair of nucleic acid probe having 3' overhang ends. The pair of probes can hybridize at adjacent positions on the template polynucleotide to form a gap of one to several bases (Backman EP-A-0439182; Segev 1990 WO 90/01069; Birkenmeyer and Armstrong 1992 J. Clin. Microbiol. 30: 3089-3094; Abravaya 1995 NAR 23:675-682). The gap LCR reaction further comprises reacting the adjacent pair of probes with a DNA polymerase and nucleotides to fill in the gap, and covalent joining with a ligase enzyme and aprataxin.

In some embodiments, a ligation detection reaction (LDR) comprises a nucleic acid amplification method in which one pair of oligonucleotide probes hybridize at adjacent positions to a target polynucleotide (Wu and Wallace 1989 Genomics 4:560; Barany 1991 PNAS 88:189-193; Wiedmann 1992 Appl Environ. Microbiol. 58:3443-3447). The hybridized oligonucleotide probes can be ligated together with ligase and aprataxin, then removed via denaturation. Multiple rounds of annealing, ligating and denaturing results in linear amplification of the target polynucleotide.

Non-limiting examples of specific applications of repetitive cycle ligation reactions include: amplification of template, detection and/or quantification of the presence of a particular nucleic acid, e.g., in a diagnostic sample, ligation sequencing, single nucleotide polymorphism (SNP) analysis, SNP genotyping, mutation detection, identification of single copy genes, detecting microsatellite repeat sequences, and DNA adduct mapping, among other things. See for example U.S. Pat. No. 4,883,750 to Whitely, U.S. Pat. No. 4,988,617 to Landegren and Hood, U.S. Pat. No. 5,476,930 to Letsinger, U.S. Pat. No. 5,593,826 to Fung, U.S. Pat. No. 5,426,180 to Kool, U.S. Pat. No. 5,871,921 to Landegren; U.S. patent publication 2004/0110213 to Namsaraev; WO 1997/31256 to Barany, WO 2001/92579 to Wenz and Schroth; Xu and Kool 1999 Nucl. Acids Res. 27: 875-881, Higgins 1979 Methods in Enzymology 68: 50-71, and Engler and Richardson 1982 In: "The Enzymes" Vol. 15, Boyer ed., Academic Press, New York, N.Y., Landegren 1988 Science 241:1077-1080, Grossman 1994 Nucl. Acids. Res. 22:4527-4534, Bi and Stambrook 1997 Nucl. Acids Res. 25:2949-51, and Zirvi 1999 Nucl. Acids Res. 27:e40

In some embodiments, a ligation reaction comprises joining together two nucleic acid ends via an enhanced ligation reaction. In some embodiments, an enhanced ligation reaction comprises joining together a first end of a first nucleic acid with a first end of a second nucleic acid. In some embodiments, a first or second nucleic acid can be in unbound (e.g., non-immobilized or in solution) or can be attached to a surface (e.g., immobilized). For example, a second end of the first and/or second nucleic acid can be attached to a surface.

In some embodiments, a 5' or 3' end can be attached to a surface. In some embodiments, a nucleic acid end can be modified for attachment to a surface. For example, a 5' or 3' end can be modified to include an amino group that can bind to a carboxylic acid compound on a surface or a particle. A 5' end can include a phosphate group for reacting with an amine-coated surface (or particle) in the presence of a carbodiimide (e.g., water soluble carbodiimide). A nucleic acid can be biotinylated at one end to bind with an avidin-like compound (e.g. streptavidin) attached to a surface.

In some embodiments, a surface can be planar, convex, concave, or any combination thereof. A surface can be porous, semi-porous or non-porous. A surface can comprise an inorganic material, natural polymers, synthetic polymers, or non-polymeric material. A surface includes a flowcell, well, groove, channel, reservoir, filter, gel or inner walls of a capillary. A surface can be coated with an acrylamide compound.

In some embodiments, a first and/or second nucleic acid can be attached to a particle. In some embodiments, a particle comprises a shape that is spherical, hemispherical, cylindrical, barrel-shaped, toroidal, rod-like, disc-like, conical, triangular, cubical, polygonal, tubular, wire-like or irregular. In some embodiments, a particle comprises an iron core or a hydrogel or agarose (e.g., Sepharose™). A In some embodiments, a particle comprises paramagnetic material. In some embodiments, a particle comprises cavitation or pores or three-dimensional scaffolds. In some embodiments, a particle comprises a coating of carboxylic acid compound or an amine compound for attaching nucleic acids. In some embodiments, a particle comprises a coating of an avidin-like compound (e.g., streptavidin) for binding biotinylated nucleic acids.

In some embodiments, a nucleic acid comprises a nucleic acid library construct. In some embodiments, one end of a nucleic acid library construct can be attached to a surface (planar surface, bead or particle). In some embodiments, a nucleic acid library construct includes any type of next generation sequencing library construct, including a fragment library (PCT/US11/24631), mate pair library (PCT/US11/54053), an RNA library (e.g., mRNA libraries, RNA-Seq libraries, whole transcriptome libraries, cell-specific RNA libraries), chromatin immunoprecipitation (ChIP) library, and methylated DNA library.

In some embodiments, beads or particles can be deposited to a surface. In some embodiments, beads or particles can be deposited to a surface of a sequencing instrument. Sequencing reagents can be delivered to the deposited beads or particles to conduct a sequencing reaction. In some embodiments, a sequencing reaction includes any next generation sequencing reaction, including: sequencing by oligonucleotide probe ligation and detection (e.g., SOLiD™ from Life Technologies, WO 2006/084131); probe-anchor ligation sequencing (e.g., Complete Genomics™ or Polonator™); sequencing-by-synthesis (e.g., Genetic Analyzer, HiSeq™ and MiSeq™ from Illumina); pyrophosphate sequencing (e.g., Genome Sequencer FLX from 454 Life Sciences); ion-sensitive sequencing (e.g., Personal Genome Machine (PGM™) and Proton™ from Ion Torrent™ Systems, Life Technologies); and single molecule sequencing platforms (e.g., HeliScope™ from Helicos).

In some embodiments, an immobilized nucleic acid library can be sequenced by employing a sequencing-byoligonucleotide-probe-ligation-and-detection sequencing reaction (e.g., SOLiD sequencing reactions, WO 2006/084132, Applied Biosystems which is now part of Life Technologies, Carlsbad, Calif.).

In some embodiments, one end of a nucleic acid library construct can be attached to a surface (e.g., Ion Sphere™ Particle, sold as a component of the Ion Xpress Template Kit (Part No. 4469001). Immobilizing nucleic acid library constructs to Ion Sphere™ Particles can be performed essentially according to the protocols provided in the Ion Xpress™ Template Kit v2.0 User Guide (Part No.: 4469004)). In some embodiments, a nucleic acid library construct includes a fragment library construct (PCT/US11/24631) or mate pair library construct (PCT/US11/54053). In some embodiments, an immobilized nucleic acid library can be sequenced via ion-sensitive or semiconductor sequencing methods, including sequencing methods and platforms for an Ion Torrent PGM™ or Proton™ sequencer (Life Technologies Corporation).

In some embodiments, an aprataxin enzyme comprises a polypeptide, or a fragment thereof, that catalyzes nucleotide hydrolase activity.

In some embodiments, an aprataxin enzyme comprises a polypeptide, or a fragment thereof, that catalyzes AMP hydrolase activity.

In some embodiments, an aprataxin enzyme comprises a polypeptide, or a fragment thereof, that catalyzes nucleophilic release of an adenylate group that is covalently linked to a terminal 5'-phosphate group.

In some embodiments, an aprataxin enzyme comprises a polypeptide, or a fragment thereof, that catalyzes removal of an adenosine-phosphate moiety that is covalently attached to a 5' terminus of a nucleic acid. For example, an adenosine-phosphate moiety includes AMP, AMP-lysine, adenine monophosphoramidate and adenosine polyphosphates (Ahel 2006 Nature 443:713-716; Takahashi 2007 Nucleic Acids Research 35:3797-3809; Kijas 2006 Journal Biol. Chem. 281:13939-13948; Rass 2007 Journal Biol. Chem. 282:9469-9474; Seidle 2005 Journal Biol. Chem. 280:20927-20931).

In some embodiments, an aprataxin enzyme can generate a terminal 5'-phosphate group on a nucleic acid.

In some embodiments, an aprataxin enzyme can exhibit a proofreading function during adenylate removal (Rass 2007 Journal Biol. Chem. 282:9469-9474).

In some embodiments, an aprataxin enzyme comprises a polypeptide having an amino acid sequence of a member of a histidine triad superfamily (or portion thereof) which include nucleotide binding proteins such as nucleotide hydrolases and transferases (Brenner 2002 Biochemistry 41:9003-9014).

In some embodiments, an aprataxin enzyme can include at least one polypeptide domain found in a naturally-occurring aprataxin enzyme, including: (i) a forkhead-associated domain (FHA) which interacts with a DNA repair/ligase complex such as ligases, polymerases, or a single-strand break repair protein XRCC1 or XRCC4 (Harris 2009 Human Mol. Gen. 18:4102-4117); a histidine triad nucleotide hydrolase domain (HIT) which catalyzes adenylate hydrolase activity (Brenner 2002 Biochemistry 41:9003-9014); and/or (iii) a zinc finger domain (ZF) which interacts with adenylated DNA to stabilize the DNA-enzyme complex (Rass 2007 Journal Biol. Chem. 282:9469-9474).

In some embodiments, an aprataxin enzyme comprises a histidine triad motif HxHxHxx, where x can be a hydrophobic amino acid. In some embodiments, a hydrophobic amino acid includes glycine, alanine, valine, leucine, iso-leucine, methionine, phenylalanine, tryptophan and proline. For example, a histidine triad motif comprises an amino acid sequence His-Val-His-Leu-His-Val-Ile (in 3-letter amino acid code).

In some embodiments, an aprataxin enzyme comprises intact subunits, biologically-active fragments, mutant variants, truncated variants, recombinant variants, fusion variants, chimeric variants, naturally-occurring aprataxins, or non-naturally occurring aprataxins. Mutant variants include amino acid substitutions, insertions, and/or deletions. In some embodiments, an aprataxin enzyme comprises naturally-occurring amino acids and/or amino acid analogs.

In some embodiments, an aprataxin enzyme can be isolated from a cell, or generated using recombinant DNA technology or chemical synthesis methods. In some embodiments, an aprataxin enzyme can be expressed in prokaryote, eukaryote, viral, or phage organisms. In some embodiments, an aprataxin enzyme can be post-translationally modified proteins or fragments thereof.

In some embodiments, an aprataxin enzyme can be a recombinant protein which is produced by a suitable expression vector/host cell system. An aprataxin can be encoded by a suitable recombinant expression vector carrying an inserted nucleotide sequence of an aprataxin enzyme, or portion thereof. An aprataxin nucleotide sequence can be operably linked to a suitable expression vector. An aprataxin nucleotide sequence can be inserted in-frame into the suitable expression vector. A suitable expression vector can replicate in a phage host, or a prokaryotic or eukaryotic host cell. A suitable expression vector can replicate autonomously in a host cell, or can be inserted into a host cell's genome and be replicated as part of a host genome. A suitable expression vector can carry a selectable marker that confers resistance to drugs (e.g., kanamycin, ampicillin, tetracycline, chloramphenicol, or the like) or a requirement for a nutrient. A suitable expression vector can have one or more restriction sites for inserting a nucleic acid molecule of interest. A suitable expression vector can include expression control sequences for regulating transcription and/or translation of the encoded sequence. An expression control sequence can include: promoters (e.g., inducible or constitutive), enhancers, transcription terminators, and/or secretion signals. An expression vector can include a plasmid, cosmid, or phage vector. An expression vector can enter a host cell which can replicate the vector, produce an RNA transcript of the inserted sequence, and/or produce protein encoded by the inserted sequence. A recombinant aprataxin enzyme can include an affinity tag for enrichment or purification, including a biotin, poly-His, GST and/or HA sequence tag. Methods for preparing suitable recombinant expression vectors and expressing the RNA and/or protein encoded by the inserted sequences are well known in the art (Sambrook et al, in: *Molecular Cloning* (1989)).

A polypeptide having aprataxin activity can include without limitation bacterial aprataxins, eukaryotic aprataxins, archaeal aprataxins, viral aprataxins and phage aprataxins. An aprataxin enzyme can be commercially-available. In some embodiments, an aprataxin enzyme comprises monkey (NCBI accession No. NP001253363), dog (NCBI accession No. NP001003355), rat (NCBI accession No. NP683687), cattle (NCBI accession No. NP872595), pig (NCBI accession No. NP998899), zebrafish (NCBI accession No. NP999894), or frog aprataxin (NCBI accession No. NP001082689). In some embodiments, an aprataxin enzyme comprises human aprataxin (FIG. 2A, SEQ ID NO:2). A polypeptide having aprataxin activity can be encoded by a nucleic acid having a nucleotide sequence as shown in FIG.

2B (SEQ ID NO:3). It will be appreciated by the skilled artisan that other nucleotide sequences that encode an apratoxin polypeptide are possible given the degenerate genetic code.

In some embodiments, a ligase enzyme comprises a polypeptide, or fragment thereof, that catalyzes phosphodiester bond formation between a terminal 5' phosphate end and a terminal 3'OH end to join together the two nucleic acid ends. In some embodiments, a ligase enzyme comprises a DNA ligase or RNA ligase.

In some embodiments, a ligase enzyme can catalyze closing a single-stranded nick in a DNA duplex or joining together two ends of two nucleic acid strands or joining together two ends of a single nucleic acid strand (e.g., circularization).

In some embodiments, a ligase enzyme can catalyze joining together blunt-ends or overhang-ends.

In some embodiments, a ligase enzyme comprises a polypeptide (or fragment thereof) that exhibits ATP-dependent or NAD-dependent ligase activity.

In some embodiments, a ligase enzyme comprises a mesophilic or thermophilic ligase enzyme. In some embodiments, a thermostable ligase enzyme can exhibit ligase activity at about 40-65° C., or about 65-85° C., or about 85-99° C. or higher temperature ranges.

In some embodiments, a ligase enzyme comprises a high ligation fidelity enzyme. For example, a ligase can discriminate the degree of hybridization between opposing nucleic acid strands in a duplex.

In some embodiments, a ligase can have one or more of the following activities: (1) nucleophilic attack on ATP or NAD resulting in release of PPi or NMN and formation of a covalent ligase-adenylate intermediate; (2) transferring the adenylate to the 5'-end of a 5'-phosphate-terminated DNA strand to form a DNA-adenylate complex (e.g., the 5'-phosphate oxygen of the DNA strand attacks the phosphorus of ligase-adenylate); and/or (3) formation of a covalent bond joining the polynucleotide termini and liberation of AMP (e.g., by the attack by the 3'-OH on DNA-adenylate).

Optionally, a ligase can mediate any one or more of the following bond transformations: from phosphoanhydride (ATP) to phosphoramidate (ligase-adenylate); from phosphoramidate (ligase-adenylate) to phosphoanhydride (DNA-adenylate); or from phosphoanhydride (DNA-adenylate) to phosphodiester (sealed DNA).

In some embodiments, a ligase enzyme comprises an E. coli DNA ligase, Taq DNA ligase, 9° N DNA ligase, or T4 DNA ligase.

In some embodiment, a ligase enzyme comprises a small footprint ligase enzyme which can ligate short nucleic acids.

In some embodiments, a small footprint ligase can join together a polynucleotide to an oligonucleotide that is 8, 7, 6, 5, 4, 3 or 2 nucleotides in length. Ligation of such oligonucleotides can be to oligonucleotides of the same length or of different length or to a polynucleotide. For example, an oligonucleotide of 2 or 3 nucleotides in length can be ligated to an oligonucleotide of 2, 3, 4, 5, 6, 7, 8 or more nucleotides in length or to longer oligonucleotides or to a polynucleotide.

Exemplary ligases can comprise a polypeptide sequence that is homologous to or a variant of a known ligase or small footprint ligase sequence or any portion thereof. Exemplary ligases and small footprint ligases optionally have amino acid sequence identity of at least 70%, optionally at least 85%, optionally at least 90, 95%, 97% or 99%, with a known ligase or known small footprint ligase.

Representative examples of small footprint ligases include a Hin DNA ligases (e.g., DLX, DLXd, and DLXd2 ligases), a Chlorella Virus ligase (FIG. 3, SEQ ID NO:3), and MnM ligase (FIG. 4, SEQ ID NO:4).

In some embodiments, a small footprint ligase can be derived from a Hin DNA ligase (e.g., DLX, DLXd or DLXd2) (FIGS. 5-8, SEQ ID NOS:5-8, respectively) or any fragment or variant thereof that still retains one or more mutant residues shown in any of FIGS. 3-8 (SEQ ID NOS:3-8, respectively), and/or has one or more C-terminal amino acids deleted, e.g., 22 C-terminal amino acids deleted. For example, a mutant Hin DNA ligase can be at least 70% identical to Hin D ligase sequence provided in any of FIGS. 5-8 (SEQ ID NOS:5-8, respectively) or in GenBank Accession No. P44121, which ligase comprises an amino acid mutation at position 193 of the Hin D ligase sequence provided in FIGS. 5-8 (SEQ ID NOS:5-8, respectively) or in GenBank Accession No. P44121. Optionally the amino acid mutation consists of changing the glycine at position 193 to aspartic acid or glutamic acid.

In some embodiments, a small footprint ligase can be derived from a Chlorella virus (ChVLig) (Ho 1997 J Virol, 71(3):1931-19374) or a Paramecium Bursaria Chlorella Virus ligase (PBCV ligase) (Odell and Shuman 1999 Journal of Biol. Chem. 274:14032-14039) or a functional fragment or variant thereof. For example a small footprint ligase can comprise any one or more domains characteristic of a ligase, e.g., an N-terminal nucleotidyltransferase (NTase) domain and/or a C-terminal oligonucleotide binding domain (OB domain). In some embodiments, an oligonucleotide binding domain optionally comprises a five-stranded antiparallel beta-barrel plus an alpha-helix. In some embodiments, the N-terminal nucleotidyltransferase domain includes an adenylate-binding pocket composed of the six peptide motifs that define the covalent NTase enzyme family of polynucleotide ligases.

Optionally, the N-terminal nucleotidyltransferase domain can comprise any one or more of the ligase amino acid motifs I, Ia, III, IIIa, IV, V, and VI. For example, Motif I (e.g., KxDGxR or a "KXDG" motif) optionally comprises a lysine. Exemplary sequences for each motif in a Chlorella virus ligase comprise ATPKIDGIR (motif I), SRT (motif Ia), EGSDGEIS (motif III), YWFDY (motif IIIa), EGVMIR (motif IV), LLKMK (motif V).

In some embodiments, a Motif 1 comprises a lysine residue. Other examples of motif I include CELKLDGLA, VEHKVDGLS, CEPKLDGLA, CELKLDGVA, AEIKYDGVR, CEYKYDGQR, VDYKYDGER, FEIKYDGAR, FEGKWDGYR, AREKIHGTN, ACEKVHGTN, ILTKEDGSL, and VEEKVDGYN.

Examples of motif Ia include TRG, SRT, SRR, SRN, SRS, KRT, KRS, SKG and TRG.

Examples of motif III include LEVRGEVF, VEVRGECY, LEVRGEVY, LEARGEAF, FMLDGELM, EGSDGEIS, FILDTEAV, FIIEGEIV, AIVEGELV, VVLDGEAV, YQVFGEFA, LVLNGELF, FTANFEFV and LILVGEMA.

Examples of motif IIIa include FCYGV, FLYTV, TFYAL, ICHGL, NAYGI, FVYGL, KLYAI, YWFDY, YAFDI, FLFDL, NLFDV, WAFDL, YVFDI, FAFDI, ILLNA, and FLFDV.

Examples of motif IV include DGVVIK, DGIVIK, DGVVVK, DGTVLK, EGLIVK, EGVMIR, EGLMVK, EGVMVK, EGLMAK, EGVIAK, EGYVLK, EGVVIR, EGYVAV, and EGIIMK.

Examples of motif V include AVAFK, AIAYK, ALAYK, AIAYK, WWKMK, LLKMK, WLKLK, WIKLK, WLKIK, WVKDK, AIKCK, IIKLR, HFKIK and IVKYV.

In some embodiments, small footprint ligases include *Paramecium bursaria Chlorella* virus (PBCV) ligase enzyme. In some embodiments, the PBCV ligase enzyme comprises an amino acid sequence shown in FIG. 3 (SEQ ID NO:3). In some embodiments, the aprataxin enzyme comprises an amino acid sequence shown in FIG. 2A. In some embodiments, the PBCV ligase enzyme exhibits activity of a small footprint ligase enzyme. In some embodiments, the nick is contacted with about 0.001-2 mg/ml of PBCV ligase enzyme and about 0.001-2 mg/ml of aprataxin enzyme. In some embodiments, the nick is contacted with about 0.01-1 mg/ml of PBCV ligase enzyme and about 0.01-1 mg/ml of aprataxin enzyme. In some embodiments, the PBVC ligase and aprataxin can be stored in a solution comprising about 1-25 mM Tris (pH about 7.5), about 0.001-0.5 EDTA, about 10-200 mM KCl, about 0.001-2 mM DTT, about 0.001-0.5% Tween 20, and about 10-75% glycerol. In some embodiments, a SOLiD sequencing reaction can be conducted with nucleic acid-templated beads, labeled oligonucleotide probes (that can hybridize to the nucleic acid template to form nicks), PBCV ligase enzyme, and aprataxin enzyme under conditions suitable for ligation reactions.

In some embodiments, small footprint ligases include those described in U.S. Serial Nos. 61/433,488 filed on Jan. 17, 2011, U.S. 61/433,502, filed on Jan. 17, 2011, U.S. 61/474,168, filed on Apr. 11, 2011, U.S. 61/474,205, filed on Apr. 11, 2011, and published PCT application No. PCT/US2012/021465, filed on Jan. 17, 2012, all these references are hereby incorporated by reference in their entireties.

In some embodiments, a small footprint ligase comprises an RNA-capping enzyme, or does not comprise an RNA-capping enzyme.

In some embodiments, methods for enhancing a nucleic acid ligation reaction comprise joining together nucleic acid ends (ends of nucleic acids, oligonucleotides or polynucleotides). In some embodiments, nucleic acids comprise single-stranded or double-stranded nucleic acids. In some embodiments, nucleic acids comprise DNA, RNA or chimeric RNA/DNA. In some embodiments, nucleic acids comprise isolated nucleic acids in any form including chromosomal, genomic, organellar (e.g., mitochondrial, chloroplast or ribosomal), recombinant molecules, cloned, sub-cloned, amplified (e.g., PCR amplified), cDNA, RNA such as precursor mRNA or mRNA, oligonucleotide, or any type of nucleic acid library. In some embodiments, nucleic acids can be isolated from any source including from organisms such as prokaryotes, eukaryotes (e.g., humans, plants and animals), fungus, and viruses; cells; tissues; normal or diseased cells or tissues; organs; body fluids; environmental samples; culture samples; or synthesized nucleic acid molecules prepared using recombinant molecular biology or chemical synthesis methods. In some embodiments, nucleic acids can be chemically synthesized to include any type of natural and/or analog nucleic acid. In some embodiments, nucleic acids can be isolated from a formalin-fixed tissue, or from a paraffin-embedded tissue, or from a formalin-fix paraffin-embedded (FFPE) tissue. In some embodiments, amplified nucleic acids can be generated by one or more cycles of a template walking reaction comprising primer extension of a primer hybridized to a template strand to produce an extended strand, and partial or incomplete denaturation of the extended strand from the template stand (U.S. non-provisional application Ser. No. 13/328,844, filed on Dec. 16, 2011).

In some embodiments, nucleic acids joined together with ligase and aprataxin can be sequenced using methods that detect one or more byproducts of nucleotide incorporation. The detection of polymerase extension by detecting physicochemical byproducts of the extension reaction, can include pyrophosphate, hydrogen ion, charge transfer, heat, and the like, as disclosed, for example, in Pourmand et al, Proc. Natl. Acad. Sci., 103: 6466-6470 (2006); Purushothaman et al., IEEE ISCAS, IV-169-172; Rothberg et al, U.S. Patent Publication No. 2009/0026082; Anderson et al, Sensors and Actuators B Chem., 129: 79-86 (2008); Sakata et al., Angew. Chem. 118:2283-2286 (2006); Esfandyapour et al., U.S. Patent Publication No. 2008/01666727; and Sakurai et al., Anal. Chem. 64: 1996-1997 (1992).

Reactions involving the generation and detection of ions are widely performed. The use of direct ion detection methods to monitor the progress of such reactions can simplify many current biological assays. For example, template-dependent nucleic acid synthesis by a polymerase can be monitored by detecting hydrogen ions that are generated as natural byproducts of nucleotide incorporations catalyzed by the polymerase. Ion-sensitive sequencing (also referred to as "pH-based" or "ion-based" nucleic acid sequencing) exploits the direct detection of ionic byproducts, such as hydrogen ions, that are produced as a byproduct of nucleotide incorporation. In one exemplary system for ion-based sequencing, the nucleic acid to be sequenced can be captured in a microwell, and nucleotides can be floated across the well, one at a time, under nucleotide incorporation conditions. The polymerase incorporates the appropriate nucleotide into the growing strand, and the hydrogen ion that is released can change the pH in the solution, which can be detected by an ion sensor. This technique does not require labeling of the nucleotides or expensive optical components, and allows for far more rapid completion of sequencing runs. Examples of such ion-based nucleic acid sequencing methods and platforms include the Ion Torrent PGM™ or Proton™ sequencer (Life Technologies Corporation).

In some embodiments, one or more nucleic acid fragments produced using the methods, systems and kits of the present teachings can be used as a substrate for a biological or chemical reaction that is detected and/or monitored by a sensor including a field-effect transistor (FET). In various embodiments the FET is a chemFET or an ISFET. A "chemFET" or chemical field-effect transistor, is a type of field effect transistor that acts as a chemical sensor. It is the structural analog of a MOSFET transistor, where the charge on the gate electrode is applied by a chemical process. An "ISFET" or ion-sensitive field-effect transistor, is used for measuring ion concentrations in solution; when the ion concentration (such as H+) changes, the current through the transistor will change accordingly. A detailed theory of operation of an ISFET is given in "Thirty years of ISFETOLOGY: what happened in the past 30 years and what may happen in the next 30 years," P. Bergveld, Sens. Actuators, 88 (2003), pp. 1-20.

In some embodiments, the FET may be a FET array. As used herein, an "array" is a planar arrangement of elements such as sensors or wells. The array may be one or two dimensional. A one dimensional array can be an array having one column (or row) of elements in the first dimension and a plurality of columns (or rows) in the second dimension. The number of columns (or rows) in the first and second dimensions may or may not be the same. The FET or array can comprise 102, 103, 104, 105, 106, 107 or more FETs.

In some embodiments, one or more microfluidic structures can be fabricated above the FET sensor array to provide for containment and/or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, and/or concentration in the given well. In some embodiments, there can be a 1:1 correspondence of FET sensors and reaction wells.

Microwells or reaction chambers are typically hollows or wells having well-defined shapes and volumes which can be manufactured into a substrate and can be fabricated using conventional microfabrication techniques, e.g. as disclosed in the following references: Doering and Nishi, Editors, Handbook of Semiconductor Manufacturing Technology, Second Edition (CRC Press, 2007); Saliterman, Fundamentals of BioMEMS and Medical Microdevices (SPIE Publications, 2006); Elwenspoek et al, Silicon Micromachining (Cambridge University Press, 2004); and the like. Examples of configurations (e.g. spacing, shape and volumes) of microwells or reaction chambers are disclosed in Rothberg et al, U.S. patent publication 2009/0127589; Rothberg et al, U.K. patent application GB24611127.

In some embodiments, the biological or chemical reaction can be performed in a solution or a reaction chamber that is in contact with or capacitively coupled to a FET such as a chemFET or an ISFET. The FET (or chemFET or ISFET) and/or reaction chamber can be an array of FETs or reaction chambers, respectively.

In some embodiments, a biological or chemical reaction can be carried out in a two-dimensional array of reaction chambers, wherein each reaction chamber can be coupled to a FET, and each reaction chamber is no greater than 10 $\mu m^3$ (i.e., 1 pL) in volume. In some embodiments each reaction chamber is no greater than 0.34 pL, 0.096 pL or even 0.012 pL in volume. A reaction chamber can optionally be 22, 32, 42, 52, 62, 72, 82, 92, or 102 square microns in cross-sectional area at the top. Preferably, the array has at least 102, 103, 104, 105, 106, 107, 108, 109, or more reaction chambers. In some embodiments, the reaction chambers can be capacitively coupled to the FETs.

FET arrays as used in various embodiments according to the disclosure can be fabricated according to conventional CMOS fabrications techniques, as well as modified CMOS fabrication techniques and other semiconductor fabrication techniques beyond those conventionally employed in CMOS fabrication. Additionally, various lithography techniques can be employed as part of an array fabrication process.

Exemplary FET arrays suitable for use in the disclosed methods, as well as microwells and attendant fluidics, and methods for manufacturing them, are disclosed, for example, in U.S. Patent Publication No. 20100301398; U.S. Patent Publication No. 20100300895; U.S. Patent Publication No. 20100300559; U.S. Patent Publication No. 20100197507, U.S. Patent Publication No. 20100137143; U.S. Patent Publication No. 20090127589; and U.S. Patent Publication No. 20090026082, which are incorporated by reference in their entireties. Examples of an array can include Ion Torrent™ System arrays, such as the 314™, 316™ and 318™ Chips (Life Technologies) used in conjunction with an Ion Torrent™ PGM or Proton™ Sequencer (Life Technologies, Part No. 4462917).

In one aspect, the disclosed methods, compositions, systems, apparatuses and kits can be used for carrying out label-free nucleic acid sequencing, and in particular, ion-based nucleic acid sequencing. The concept of label-free detection of nucleotide incorporation has been described in the literature, including the following references that are incorporated by reference: Rothberg et al, U.S. patent publication 2009/0026082; Anderson et al, Sensors and Actuators B Chem., 129: 79-86 (2008); and Pourmand et al, Proc. Natl. Acad. Sci., 103: 6466-6470 (2006). Briefly, in nucleic acid sequencing applications, nucleotide incorporations are determined by measuring natural byproducts of polymerase-catalyzed extension reactions, including hydrogen ions, polyphosphates, PPi, and Pi (e.g., in the presence of pyrophosphatase).

In some embodiments, the disclosure relates generally to methods for joining together nucleic acids with ligase and aprataxin to generate a nucleic acid construct that can be sequenced using hydrogen ion-sensitive sequencing methods.

In some embodiments, the nucleic acid construct can be sequenced using an ion-sensitive sequencing method. In some embodiments, the sequencing method is performed by incorporating one or more nucleotides in a template-dependent fashion into a newly synthesized nucleic acid strand.

Optionally, the methods can further include producing one or more ionic byproducts of such nucleotide incorporation.

In some embodiments, the methods can further include detecting the incorporation of the one or more nucleotides into the sequencing primer. Optionally, the detecting can include detecting the release of hydrogen ions.

In another embodiment, the disclosure relates generally to a method for sequencing a nucleic acid, comprising: (a) producing a nucleic acid construct according to the methods disclosed herein; (b) disposing a plurality of nucleic acid constructs into a plurality of reaction chambers, wherein one or more of the reaction chambers are in contact with a field effect transistor (FET). Optionally, the method further includes contacting at least one of the nucleic acid constructs disposed into one of the reaction chambers with a polymerase, thereby synthesizing a new nucleic acid strand by sequentially incorporating one or more nucleotides into a nucleic acid molecule. Optionally, the method further includes generating one or more hydrogen ions as a byproduct of such nucleotide incorporation. Optionally, the method further includes detecting the incorporation of the one or more nucleotides by detecting the generation of the one or more hydrogen ions using the FET.

In some embodiments, the detecting includes detecting a change in voltage and/or current at the at least one FET within the array in response to the generation of the one or more hydrogen ions.

In some embodiments, the FET can be selected from the group consisting of: ion-sensitive FET (isFET) and chemically-sensitive FET (chemFET).

One exemplary system involving sequencing via detection of ionic byproducts of nucleotide incorporation is the Ion Torrent PGM™ or Proton™ sequencer (Life Technologies), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™ or Proton™ sequencer detects the nucleotide incorporations by detecting the hydrogen ion byproducts of the nucleotide incorporations. The Ion Torrent PGM™ or Proton™ sequencer can include a plurality of nucleic acid templates to be sequenced, each template disposed within a respective sequencing reaction well in an array. The wells of the array can each be coupled to at least one ion sensor that can detect the release of $H^+$ ions or changes in solution pH produced as a byproduct of nucleotide incorporation. The ion sensor comprises a field effect transistor (FET) coupled to an ion-sensitive detection layer that can sense the presence of $H^+$ ions or changes in solution pH. The ion sensor can provide output signals indicative of nucleotide incorporation which can be represented as voltage changes whose magnitude correlates with the $H^+$ ion concentration in a respective well or reaction chamber. Different nucleotide types can be flowed serially into the reaction chamber, and can be incorporated by the polymerase into an extending primer (or polymerization site) in an order determined by the sequence of the template. Each nucleotide incorporation can be accompanied by the release of $H^+$ ions in the reaction well, along with a concomitant change in the localized pH. The release of $H^+$ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously. Further details regarding the compositions, design and operation of the Ion Torrent PGM™ or Proton™ sequencer can be found, for example, in U.S. patent application Ser. No. 12/002,781, now published as U.S. Patent Publication No. 2009/0026082; U.S. patent application Ser. No. 12/474,897, now published as U.S. Patent Publication No. 2010/0137143; and U.S. patent application Ser. No. 12/492,844, now published as U.S. Patent Publication No. 2010/0282617, all of which applications are incorporated by reference herein in their entireties.

In some embodiments, the disclosure relates generally to use of nucleic acid constructs produced using any of the methods, systems and kits of the present disclosure in methods of ion-based sequencing. Use of such nucleic acid constructs in ion-based sequencing reactions can be advantageous because the methods of the disclosure permit isolation of polynucleotides (e.g., tags) of a desired size that can be selected to match the read length capacity of the ion-based sequencing system.

In a typical embodiment of ion-based nucleic acid sequencing, nucleotide incorporations can be detected by detecting the presence and/or concentration of hydrogen ions generated by polymerase-catalyzed extension reactions. In one embodiment, templates each having a primer and polymerase operably bound can be loaded into reaction chambers (such as the microwells disclosed in Rothberg et al, cited herein), after which repeated cycles of nucleotide addition and washing can be carried out. In some embodiments, such templates can be attached as clonal populations to a solid support, such as a particle, bead, or the like, and said clonal populations are loaded into reaction chambers. As used herein, "operably bound" means that a primer is annealed to a template so that the primer's 3' end may be extended by a polymerase and that a polymerase is bound to such primer-template duplex, or in close proximity thereof so that binding and/or extension takes place whenever nucleotides are added.

In each addition step of the cycle, the polymerase can extend the primer by incorporating added nucleotide only if the next base in the template is the complement of the added nucleotide. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the reaction chamber. The production of hydrogen ions is monotonically related to the number of contiguous complementary bases in the template (as well as the total number of template molecules with primer and polymerase that participate in an extension reaction). Thus, when there are a number of contiguous identical complementary bases in the template (i.e. a homopolymer region), the number of hydrogen ions generated, and therefore the magnitude of the local pH change, can be proportional to the number of contiguous identical complementary bases. If the next base in the template is not complementary to the added nucleotide, then no incorporation occurs and no hydrogen ion is released. In some embodiments, after each step of adding a nucleotide, an additional step can be performed, in which an unbuffered wash solution at a predetermined pH is used to remove the nucleotide of the previous step in order to prevent misincorporations in later cycles. In some embodiments, the after each step of adding a nucleotide, an additional step can be performed wherein the reaction chambers are treated with a nucleotide-destroying agent, such as apyrase, to eliminate any residual nucleotides remaining in the chamber, which may result in spurious extensions in subsequent cycles.

In one exemplary embodiment, different kinds of nucleotides are added sequentially to the reaction chambers, so that each reaction can be exposed to the different nucleotides one at a time. For example, nucleotides can be added in the following sequence: dATP, dCTP, dGTP, dTTP, dATP, dCTP, dGTP, dTTP, and so on; with each exposure followed by a wash step. The cycles may be repeated for 50 times, 100 times, 200 times, 300 times, 400 times, 500 times, 750 times, or more, depending on the length of sequence information desired.

In some embodiments, sequencing can be performed with an Ion Torrent™ PGM™ or Proton™ sequencer. For example, nucleic acid constructs prepared as disclosed herein can be clonally amplified on Ion Sphere™ Particles as part of the Ion Xpress™ Template Kit (Life Technologies Part No. 4469001). Template preparation can be performed essentially accordingly to the protocols provided in the Ion Xpress™ Template Kit v2.0 User Guide (Life Technologies, Part No. 4469004). The amplified DNA can then be sequenced on the Ion PGM™ sequencer (Ion Torrent™, Life Technologies, Part No. 4462917) essentially according to the protocols provided in the Ion Sequencing Kit v2.0 User Guide (Ion Torrent™, Life Technologies, Part No. 4469714) and using the reagents provided in the Ion Sequencing Kit (Ion Torrent™, Life Technologies, Part No. 4468997) and the Ion 314™ Chip Kit (Ion Torrent™, Life Technologies, Part No. 4462923).

In some embodiments, systems comprise at least one enzyme for DNA adenylation removal and at least one enzyme for nucleic acid ligation. In some embodiments, systems comprise at least one aprataxin enzyme and at least one ligase enzyme. In some embodiments, systems can include any combination of nucleic acid ends, at least on aprataxin enzyme and/or at least one ligase enzyme. In some embodiments, systems can further include any combination of components that may be required for aprataxin or ligase enzymatic activity, including buffers, reagents, ATP, NAD and/or ions (e.g., magnesium, manganese, cobalt, or calcium).

In some embodiments, kits comprise any combination of: buffers, reagents, ATP, NAD, ions (e.g., KCl, K-acetate, $NH_4$-acetate, K-glutamate, $NH_4Cl$, or ammonium sulfate) or cations (e.g., magnesium, manganese, cobalt, or calcium), at least one aprataxin enzyme, and/or at least one ligase enzyme. In some embodiments, a buffer can include Tris, Tricine, HEPES, MOPS, ACES, MES, or inorganic buffers such as phosphate or acetate-based buffers which can provide a pH range of about 4-12. In some embodiments, a buffer can include chelating agents such as EDTA or EGTA.

In some embodiments, a buffer can include dithiothreitol (DTT), glycerol, spermidine, BSA (bovine serum albumin) and/or Tween. Kits can further comprise test nucleic acids for conducting control reactions for enhanced ligation. In some embodiments, a kit can omit any of these components. For example, a kit can include at least one aprataxin enzyme or at least one ligase enzyme. In some embodiments, kits can include any combination of: various enzymes to conduct reactions such as nucleic acid ligation and/or DNA adenylation removal. In some embodiments, the kits can include a set of instructions and genome assembly guides can be included. Such material can be, for example, in print or in digital form.

What is claimed:

1. A method for ligating nucleic acids, comprising:
   a) forming a plurality of polynucleotide duplexes each having a nick, by (i) hybridizing a first template polynucleotide with a first and second probe oligonucleotide so that the first and second probe oligonucleotides abut each other to form a first nick, wherein the second probe oligonucleotide is labeled with a first distinctive reporter moiety, and wherein the 5' end of the first template polynucleotide is attached to a support, and (ii) hybridizing a second template polynucleotide with a third and fourth probe oligonucleotide so that the third and fourth oligonucleotides abut each other to form a second nick wherein, the fourth probe oligonucleotide is labeled with a second distinctive reporter moiety, wherein the first and second template polynucleotides include different sequences, wherein the second and fourth probe oligonucleotides include different sequences, wherein the first and second distinctive reporter moieties distinguish the different sequences of the second and fourth probe oligonucleotides respectively, and wherein the 5' end of the second template polynucleotide is attached to the support;
   b) closing the first and second nick to form a first and second ligation product respectively by conducting a nucleic acid ligation reaction with a ligase and an aprataxin enzyme that catalyzes removal of an adenylate group from a terminal 5' phosphate of a nucleic acid; and
   c) detecting the first distinctive reporter moiety thereby detecting the sequence of a portion of the first template polynucleotide that hybridizes to the second probe oligonucleotide, and detecting the second distinctive reporter moiety thereby detecting the sequence of a portion of the second template polynucleotide that hybridizes to the fourth probe oligonucleotide.

2. The method of claim 1, wherein the support comprises a planar support.

3. The method of claim 1, wherein the planar support comprises a plurality of wells arranged in an array.

4. The method of claim 1, wherein the planar support comprises 100-10$^7$ wells.

5. The method of claim 4, wherein each well is capacitively coupled to a field effect transistor (FET).

6. The method of claim 5, wherein the FET detects protons.

7. The method of claim 1, wherein the support comprises a bead.

8. The method of claim 7, further comprising depositing the bead onto an array.

9. The method of claim 8, wherein the array comprises a plurality of wells.

10. The method of claim 8, wherein the array comprises 100-10$^7$ wells.

11. The method of claim 8, wherein each well is capacitively coupled to a field effect transistor (FET).

12. The method of claim 11, wherein the FET detects pyrophosphate, hydrogen ions, charge transfer or heat.

13. The method of claim 1, wherein the aprataxin enzyme comprise the amino acid sequence according to SEQ ID NO:1.

14. The method of claim 1, wherein the ligase comprises a small footprint ligase comprising the amino acid sequence according to any one of SEQ ID NOS: 6-8.

15. The method of claim 1, wherein the first or second oligonucleotide includes an internal or terminal scissile linkage which is selected from a group consisting of a phosphoramidate, phosphorothioate, or phosphorodithiolate linkage.

16. The method of claim 1, wherein the first and second distinctive report moieties comprise different fluorophores.

17. The method of claim 1, further comprising: denaturing the first and second ligation product from the first and second polynucleotides respectively.

18. The method of claim 1, further comprising:
   c) forming a plurality of polynucleotide duplexes each having a nick, by (i) hybridizing the first template polynucleotide with a fifth probe oligonucleotide so that the first ligation product and the fifth probe oligonucleotide abut each other to form a third nick, wherein the fifth probe oligonucleotide is labeled with a third distinctive reporter moiety, and (ii) hybridizing the second template polynucleotide with a sixth probe oligonucleotide so that the second ligation product and the sixth probe oligonucleotide abut each other to form a fourth nick, wherein the sixth probe oligonucleotide is labeled with a fourth distinctive reporter moiety, wherein the third and fourth reporter moieties distinguish the different sequences of the fifth and sixth probe oligonucleotides respectively;

d) closing the third and fourth nick to form a third and fourth ligation product respectively, by conducting a nucleic acid ligation reaction with a ligase and an aprataxin enzyme that catalyzes removal of an adenylate group from a terminal 5' phosphate of a nucleic acid;

e) detecting the third distinctive reporter moiety thereby detecting the sequence of a portion of the first template polynucleotide that hybridizes to the fifth oligonucleotide, and detecting the fourth distinctive reporter moiety thereby detecting the sequence of a portion of the second template polynucleotide that hybridizes to the sixth oligonucleotide; and f) denaturing the third and fourth ligation products from the first and second polynucleotides respectively.

19. The method of claim 18, wherein the first, second, third and fourth distinctive reporter moieties comprise different fluorophores.

* * * * *